United States Patent
Burstein et al.

(10) Patent No.: US 7,422,605 B2
(45) Date of Patent: Sep. 9, 2008

(54) MOBILE BEARING KNEE PROSTHESIS

(75) Inventors: Albert Burstein, Sarasota, FL (US); Bennie W. Gladdish, Jr., Gainesville, FL (US); James Edward Hoyt, Gainesville, FL (US); Raymond Cloutier, Gainesville, FL (US); Laurent Angibaud, Ponson-Dessus (FR)

(73) Assignee: Exactech, Inc., Gainesville, FL (US)

( * ) Notice: Subject to any disclaimer, the term of this patent is extended or adjusted under 35 U.S.C. 154(b) by 625 days.

(21) Appl. No.: 10/894,146

(22) Filed: Jul. 19, 2004

(65) Prior Publication Data

US 2005/0027365 A1 Feb. 3, 2005

Related U.S. Application Data

(60) Provisional application No. 60/487,907, filed on Jul. 17, 2003, provisional application No. 60/551,369, filed on Mar. 9, 2004.

(51) Int. Cl.
*A61F 2/38* (2006.01)
(52) U.S. Cl. .............. 623/20.33; 623/20.32; 623/20.34
(58) Field of Classification Search ... 623/20.32–20.34, 623/20.29
See application file for complete search history.

(56) References Cited

U.S. PATENT DOCUMENTS

| | | | |
|---|---|---|---|
| RE29,757 E | 9/1978 | Helfet | |
| 4,205,400 A | 6/1980 | Shen et al. | |
| 4,215,439 A | 8/1980 | Gold et al. | |
| 4,224,696 A | 9/1980 | Murray et al. | |
| 4,268,920 A | 5/1981 | Engelbrecht et al. | |
| 4,538,305 A | 9/1985 | Engelbrecht et al. | |
| 4,759,767 A | 7/1988 | Lacey | |
| 4,795,468 A | 1/1989 | Hodorek et al. | |

(Continued)

FOREIGN PATENT DOCUMENTS

EP 0 189 253 A2 7/1986

(Continued)

OTHER PUBLICATIONS

International Search Report For PCT/US04/23189, Dated, Nov. 29, 2004, Listing The Following Three References: US2003/0040802 A1; US2003/0028254 A1; and US6,290,726 B1.

(Continued)

*Primary Examiner*—Bruce E Snow
*Assistant Examiner*—Megan Yarnall
(74) *Attorney, Agent, or Firm*—Greenberg Traurig, LLP

(57) ABSTRACT

In one embodiment of the present invention a mobile bearing knee prosthesis may include an interface (e.g., a spherical radius interface) comprised of a concave superior surface on a tibial tray and a convex inferior surface on a tibial insert. In another embodiment of the present invention a mobile bearing knee prosthesis may include an interface (e.g., a spherical radius interface) comprised of a convex superior surface on a tibial tray and a concave inferior surface on a tibial insert. In another embodiment of the present invention a mobile bearing knee prosthesis may include a bi-concave interface (e.g., having a "wave" like surface geometry). This "wave" like surface geometry may be at the second bearing (i.e., at the interface between a tibial insert and a tibial tray in the mobile bearing knee as opposed to the interface between the tibial insert and a femoral component).

1 Claim, 30 Drawing Sheets

U.S. PATENT DOCUMENTS

| | | | |
|---|---|---|---|
| 4,822,365 A | 4/1989 | Walker et al. |
| 4,822,366 A | 4/1989 | Bolesky |
| 4,936,853 A | 6/1990 | Fabian et al. |
| 4,950,297 A | 8/1990 | EHoy et al. |
| 4,950,298 A | 8/1990 | Gustilo et al. |
| 4,959,071 A | 9/1990 | Brown et al. |
| 4,985,037 A | 1/1991 | Petersen |
| 5,064,437 A | 11/1991 | Stock et al. |
| 5,071,438 A | 12/1991 | Jones et al. |
| 5,123,928 A | 6/1992 | Moser |
| 5,137,536 A | 8/1992 | Koshino |
| 5,152,796 A | 10/1992 | Slamin |
| 5,194,066 A | 3/1993 | Van Zile |
| 5,226,915 A | 7/1993 | Bertin |
| 5,271,737 A | 12/1993 | Baldwin et al. |
| 5,290,313 A | 3/1994 | Heldreth |
| 5,330,534 A | 7/1994 | Herrington et al. |
| 5,358,530 A | 10/1994 | Hodorek |
| 5,556,432 A | 9/1996 | Kubein-Meesenburg et al. |
| 5,556,433 A | 9/1996 | Gabriel et al. |
| 5,593,449 A | 1/1997 | Roberson, Jr. |
| 5,683,468 A * | 11/1997 | Pappas .................... 623/20.29 |
| 5,683,472 A | 11/1997 | O'Neil et al. |
| 5,776,200 A | 7/1998 | Johnson et al. |
| 5,782,920 A | 7/1998 | Colleran |
| 5,782,921 A | 7/1998 | Colleran et al. |
| 6,056,779 A | 5/2000 | Noyer et al. |
| RE37,277 E | 7/2001 | Baldwin et al. |
| 6,319,283 B1 | 11/2001 | Insall et al. |
| 6,645,251 B2 | 11/2003 | Salehi et al. |

FOREIGN PATENT DOCUMENTS

| | | |
|---|---|---|
| EP | 0498586 | 8/1992 |
| EP | 0 529 408 B1 | 12/1995 |
| FR | 2726174 | 5/1996 |
| FR | 2839256 | 11/2003 |
| FR | 2842411 | 1/2004 |
| WO | WO 96/13232 | 5/1996 |

OTHER PUBLICATIONS

English language abstract of FR2839256 from the esp@cenet database.

The Effect of Contact Area on Wear in Relation to Fixed Bearing and Mobile Bearing Knee Replacements; by Shivani Sathasivam et al.; John Wiley & Sons, Inc. J Biomed Mater Res (Appl Biomatter), 2001 pp. 282-290.

* cited by examiner

700

704
702

700

MOBILE BEARING KNEE PROSTHESIS

CROSS-REFERENCE TO RELATED APPLICATIONS

This application claims the benefit under 35 U.S.C. 119(e) of U.S. Provisional Application Ser. No. 60/487,907, filed Jul. 17, 2003 and U.S. Provisional Application Ser. No. 60/551,369, filed Mar. 9, 2004.

FIELD OF THE INVENTION

In one embodiment of the present invention a mobile bearing knee prosthesis may include an interface (e.g., a spherical radius interface) comprised of a concave superior surface on a tibial tray and a convex inferior surface on a tibial insert.

In another embodiment of the present invention a mobile bearing knee prosthesis may include an interface (e.g., a spherical radius interface) comprised of a convex superior surface on a tibial tray and a concave inferior surface on a tibial insert.

In another embodiment of the present invention a mobile bearing knee prosthesis may include a bi-concave interface (e.g., having a "wave" like surface geometry). This "wave" like surface geometry may be at the second bearing (i.e., at the interface between a tibial insert and a tibial tray in the mobile bearing knee as opposed to the interface between the tibial insert and a femoral component). Further, this "wave" like surface geometry may allow a "virtual" axis of rotation to be provided by the second bearing.

In one example (which example is intended to be illustrative and not restrictive) the tibial insert may include a polyethylene articulating surface. In another example (which example is intended to be illustrative and not restrictive) the tibial tray may include a metal articulating surface (e.g., a highly polished metal articulating surface). In another example (which example is intended to be illustrative and not restrictive) one or both of the articulating surfaces may include diamond (e.g., to improve wear characteristics on one or more mating surfaces).

For the purposes of the present application the term "rotational constraint" is intended to refer to essentially stopping rotation of an object at a given point.

Further, for the purposes of the present application the term "rotational control" is intended to refer to exercising control over the amount of force required to rotate an object.

Further still, for the purposes of the present application the term "superior surface" is intended to be synonymous with the term "top surface".

Further still, for the purposes of the present application the term "inferior surface" is intended to be synonymous with the term "bottom surface".

BACKGROUND OF THE INVENTION

U.S. Pat. No. 6,319,283 relates to a tibial knee component with a mobile bearing. More particularly, this patent relates to an orthopaedic knee component for implanting within a proximal tibia. The orthopaedic knee component includes a tibial tray with a proximal tibial plateau and a projection extending generally orthogonal to the tibial plateau. The tibial tray also includes a distally extending stem. A bearing is coupled with the tibial plateau and has an articular bearing surface for engagement with a femoral component. The bearing is rotationally movable between a first rotational limit and a second rotational limit about an axis extending generally orthogonal to the tibial plateau. The bearing has a backing surface engaging the tibial plateau which is sized and shaped such that the backing surface is substantially entirely supported by the tibial plateau at any position during rotational movement between the first rotation limit and the second rotational limit.

U.S. Pat. No. 5,683,468 relates to a mobile bearing total joint replacement. More particularly, this patent relates to a prosthetic component provided for a condylar joint. The prosthetic component includes a platform having a bearing surface and a pair of side walls. The side walls include a pair of concave surfaces which face one another and define arcs of the same right circular cylinder. The prosthetic component also includes a plastic bearing having a bearing surface slidably engaged with the bearing surface of the platform. The bearing also includes thrust surfaces defining arcs of two right circular cylinders having radii less than the radius of the side wall surfaces of the platform. The thrust surfaces are spaced from one another to permit only limited sliding movement of the bearing in medial to lateral directions, but greater sliding movement in anterior to posterior directions.

U.S. Pat. No. 5,556,432 relates to an artificial joint. More particularly, this patent relates to an endoprothesis for the human knee joint, consisting of at least two joint parts moving with respect to each other, a joint head and a joint base, with toroidal joint surfaces, that have function surfaces with differing circular intersection contours in mutually perpendicular planes—a longitudinal plane and a transverse plane—whereby the curve ratios of the function surfaces are defined in each of the planes as either convex—convex, convex-concave, or concave—concave, and the joint geometry of the function areas to each other in each of the two planes is determined by a link chain with two link axes (dimeric link chain), which proceed through the rotation centers of the function areas with the radii of the attendant intersection contours, respectively.

U.S. Pat. No. 5,358,530 relates to a mobile bearing knee. More particularly, this patent relates to a prosthetic mobile bearing knee including a femoral implant having condyle sections attached to a femur and a tibial tray implant having a plateau attached to a tibia. The tibial tray implant has a pair of spaced apart, concavely curved plateau bearing surfaces for cooperation and sliding with convexly curved surfaces on a tibial bearing. The tibial tray plateau bearing surfaces are shaped to create a gradually increasing resistance to sliding and rotational movement of the tibial bearing. The tibial bearing that interfits between the femoral and tibial tray implants is constructed in one or two portions.

U.S. Pat. No. 4,224,696 relates to a prosthetic knee. More particularly, this patent relates to a prosthetic knee having as its component parts a femoral implant, a tibial implant, and a meniscal plate disposed between the implants. Knee flexion and extension is permitted by compoundly curved condyle surfaces of the femoral implant, which resemble corresponding surfaces of a natural knee, and correspondingly shaped convex bearing surfaces in the meniscal plate. All other motions of the prosthetic knee take place at the interface between the meniscal plate and tibial implant. This interface is defined by a continuous, concave, spherically shaped surface in the upwardly facing plateau of the tibial implant and a corresponding, continuous, convex spherical surface of the meniscal plate. The components are biased into mutual engagement along the cooperating concave and convex surfaces by the natural ligaments which surround the prosthetic knee. The continuous biased engagement of the cooperating convex and concave surfaces of the prosthetic knee assure its stability.

Figure 1A:
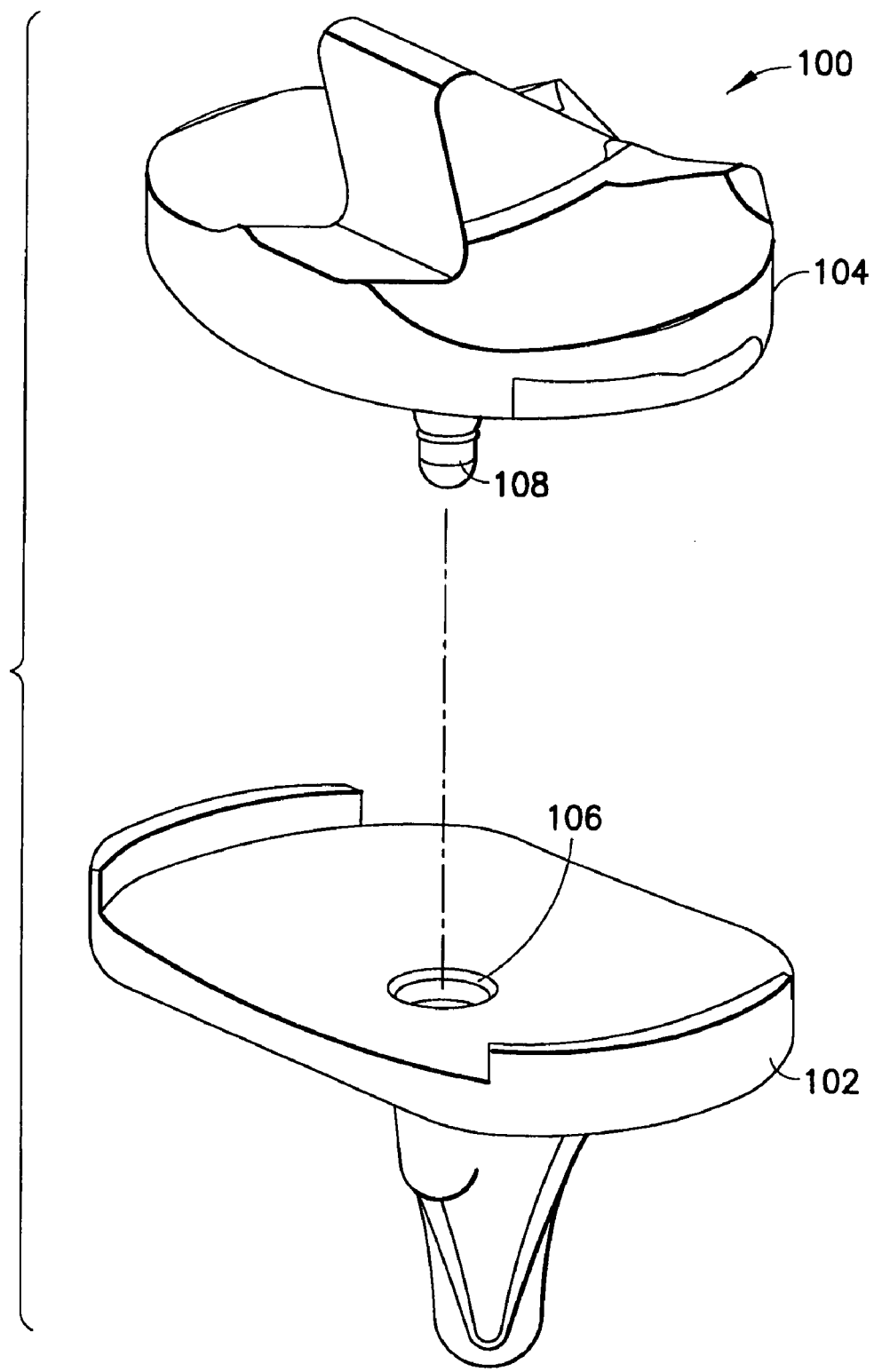
FIG. 1A shows a perspective view of a mobile bearing knee prosthesis according to an embodiment of the present invention.
Figure 1B:
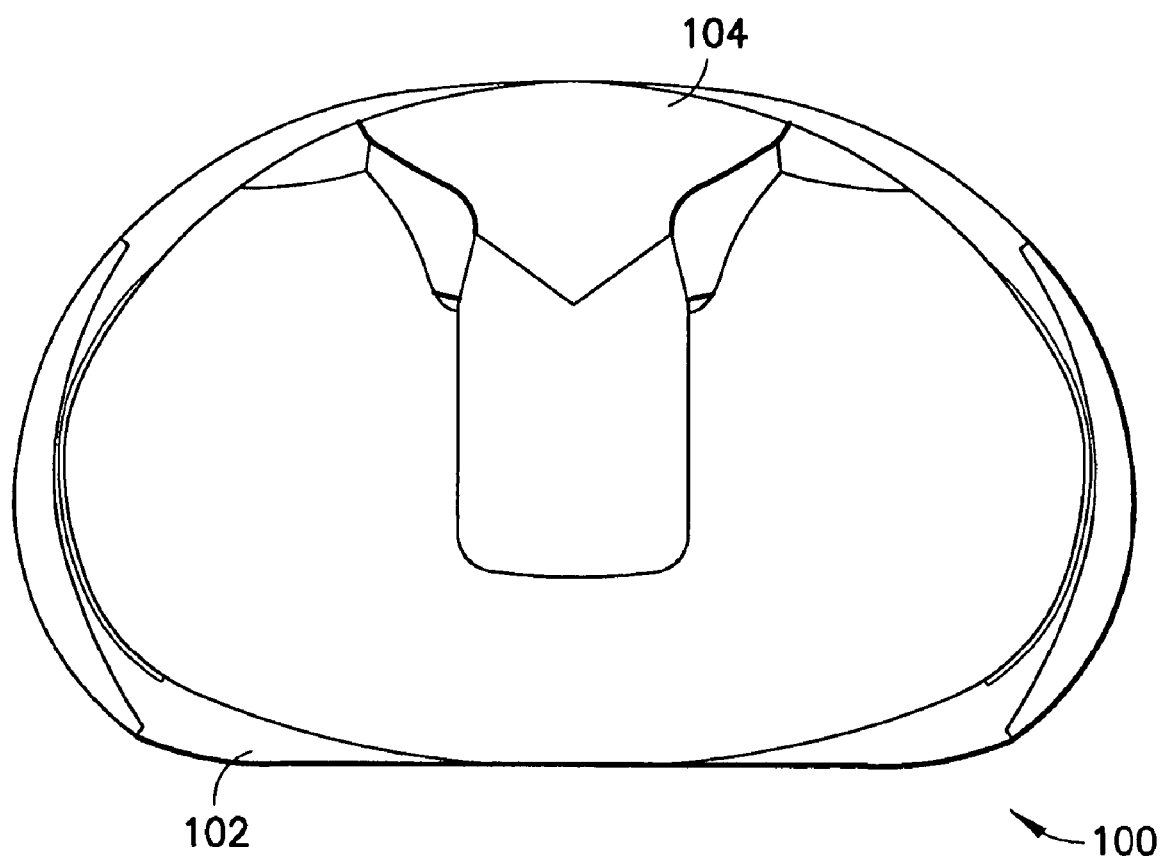
FIG. 1B shows a top plan view of the mobile bearing knee prosthesis of FIG. 1A.
Figure 1C:
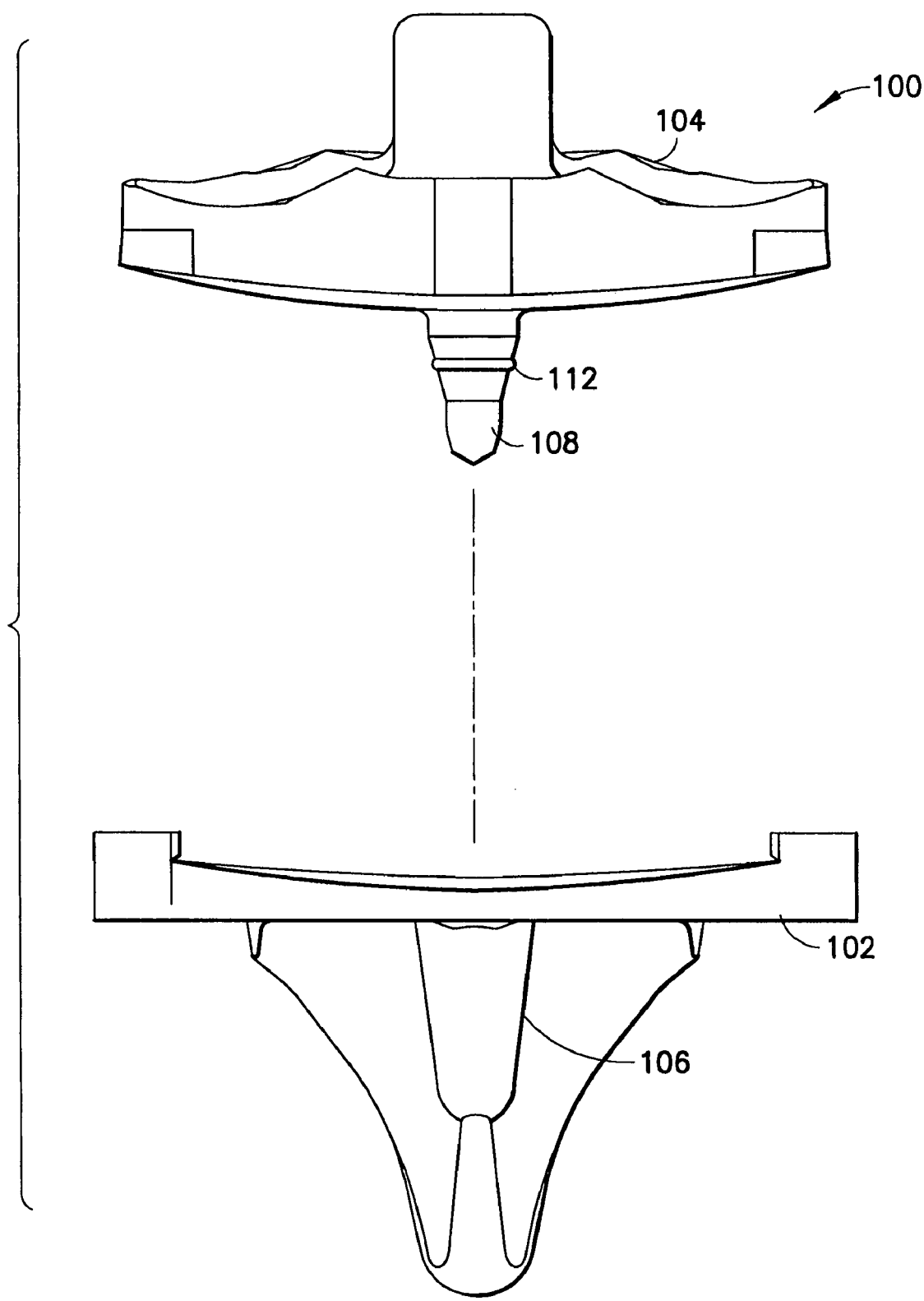
FIG. 1C shows a side view of the mobile bearing knee prosthesis of FIG. 1A.
Figure 1D:
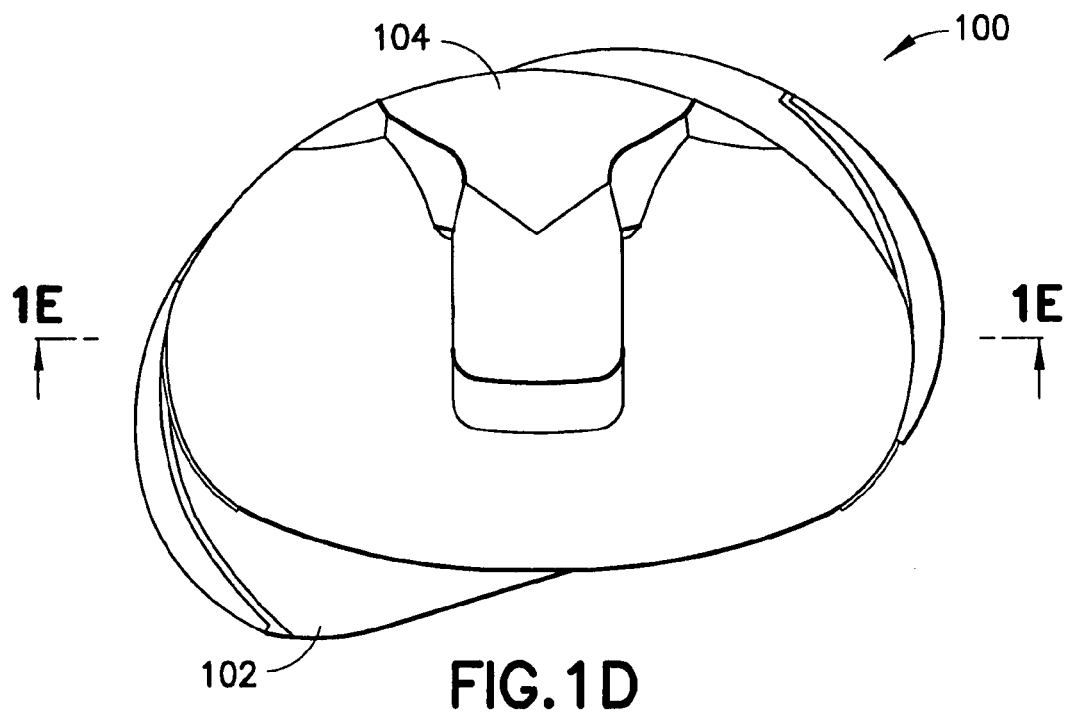
FIG. 1D shows another top plan view of the mobile bearing knee prosthesis of FIG. 1A.
Figure 1E:
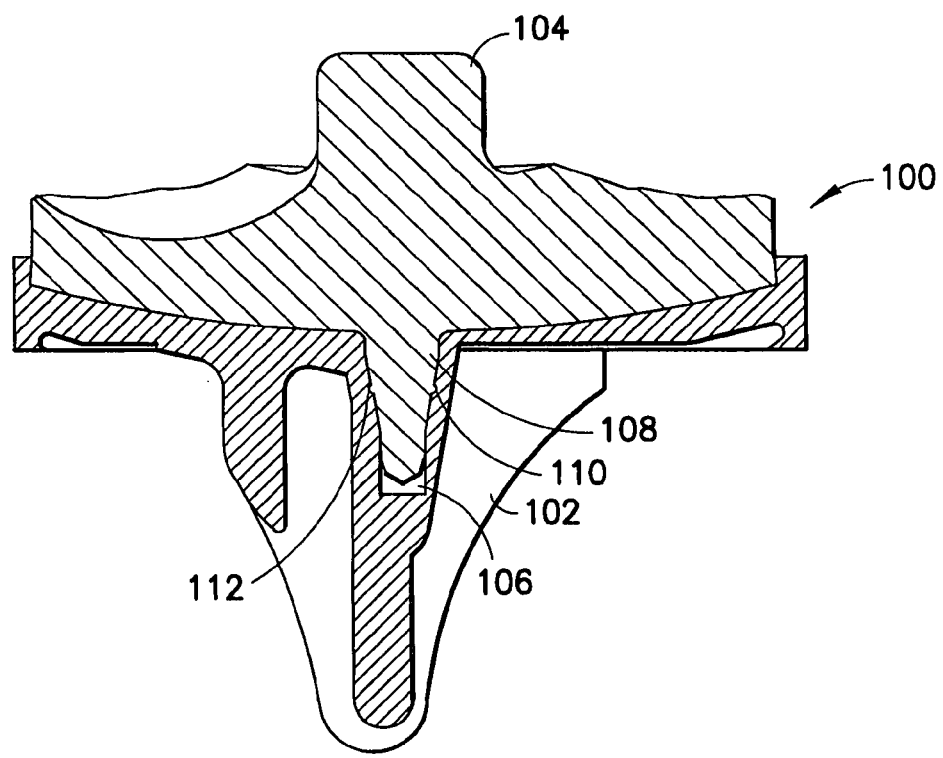
FIG. 1E shows a cross section taken along line A-A of FIG. 1D.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

In one embodiment a mobile bearing knee prosthesis may include an interface (e.g., a spherical radius interface) comprised of a concave superior surface on a tibial tray and a convex inferior surface on a tibial insert. In another embodiment a mobile bearing knee prosthesis may include an interface (e.g., a spherical radius interface) comprised of a convex superior surface on a tibial tray and a concave inferior surface on a tibial insert. Of note, such a spherical radius may have an inherent tendency to self-align.

In one example (which example is intended to be illustrative and not restrictive) the tibial insert may include a polyethylene articulating surface. In another example (which example is intended to be illustrative and not restrictive) the tibial tray may include a metal articulating surface (e.g., a highly polished metal articulating surface). In another example (which example is intended to be illustrative and not restrictive) one or both of the articulating surfaces may include diamond (e.g., to improve wear characteristics on one or more mating surfaces).

In another embodiment of a mobile bearing knee prosthesis the interface may have a pivoting location. In one example (which example is intended to be illustrative and not restrictive) the pivoting location may be defined by a female feature (e.g., cylinder, cone or combination) that mates with a male feature (e.g., a post). The pivoting location may be in the center of the interface or the pivoting location may be offset from the center of the interface in one or more of a medial, lateral, anterior and/or posterior directions.

In another embodiment of a mobile bearing knee prosthesis a locking feature may be provided to help prevent lift-off of the tibial insert. In one example (which example is intended to be illustrative and not restrictive) the locking feature may be provided by a male feature (e.g., a post) working in combination with a female feature (e.g., cylinder, cone or combination) to help prevent lift-off of an articulating surface (e.g., a polyethylene articulating surface).

In another embodiment of a mobile bearing knee prosthesis anterior/posterior translation and/or medial/lateral translation may be provided by utilizing a female feature (e.g., cylinder, cone or combination) which is enlarged to allow for additional movement in one or more desired planes.

In another embodiment of a mobile bearing knee prosthesis rotational constraint and/or control may be provided by medial and/or lateral rails that interfere and/or wedge with a tibial insert as the tibial insert rotates to a specific angular displacement (the interference and/or wedging may occur at one or both rails). Further, to aid in containment of the tibial insert, a groove may be provided in one or both rails and a mating feature may be provided on the tibial insert.

In another embodiment of a mobile bearing knee prosthesis rotational constraint and/or control may be provided by using a male feature (e.g., a post) as a spring (e.g., a torsion spring) such that a constraining member (e.g., a cross-pin) can be inserted into a receiving member (e.g., a V-groove) in the male feature.

In another embodiment of a mobile bearing knee prosthesis rotational constraint and/or control may be provided by using an ellipsoid surface at the rotational interface.

Referring now to FIGS. 1A-1E, Mobile Bearing Knee Prosthesis 100 may include Tibial Tray 102, Tibial Insert 104 and Femoral Component (not shown) which interfaces with Tibial Insert 104.

In one example (which example is intended to be illustrative and not restrictive) Mobile Bearing Knee Prosthesis 100 may include an interface (e.g., a spherical radius interface) comprised of a concave superior surface on the Tibial Tray 102 and a convex inferior surface on the Tibial Insert 104 (of note, such a spherical radius may have an inherent tendency to self-align).

In another example (which example is intended to be illustrative and not restrictive) the Tibial Insert 104 may include a polyethylene articulating surface. In another example (which example is intended to be illustrative and not restrictive) the Tibial Insert 102 may include a metal articulating surface (e.g., a highly polished metal articulating surface).

Mobile Bearing Knee Prosthesis 100 may have a pivoting location. In one example (which example is intended to be illustrative and not restrictive) the pivoting location may be defined by Cavity 106 that mates with Post 108. Post 108 may stabilize Mobile Bearing Knee Prosthesis 100 against shear forces (e.g., medial/lateral forces in the transverse plane) as well as serve as a rotational axis.

Mobile Bearing Knee Prosthesis 100 may include locking feature(s) to help prevent lift-off of the Tibial Insert 104. In one example (which example is intended to be illustrative and not restrictive) the locking feature may be provided by Indentation 110 (disposed within Cavity 106) working in conjunction with Raised Portion 112 (disposed on Post 108) (see, for example, FIG. 1E).

Further, Mobile Bearing Knee Prosthesis 100 may provide anterior/posterior translation and/or medial/lateral translation (e.g., by utilizing Cavity 106 which is enlarged to allow for additional movement in one or more desired planes). In one example (which example is intended to be illustrative and not restrictive) A/P translation may be about 4.5 mm.

Figure 2A:
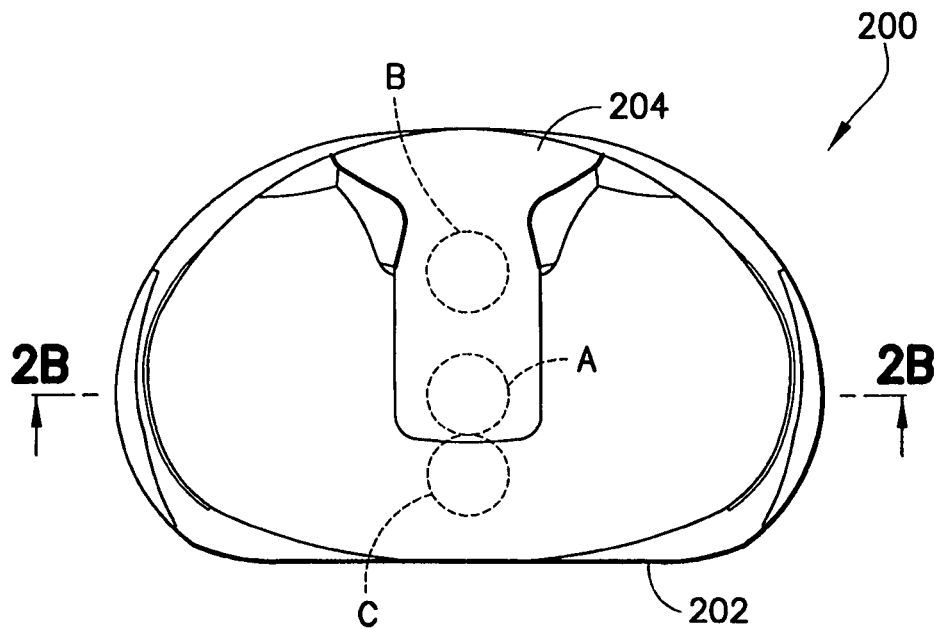
FIG. 2A shows a top plan view of a mobile bearing knee prosthesis according to another embodiment of the present invention.
Figure 2B:
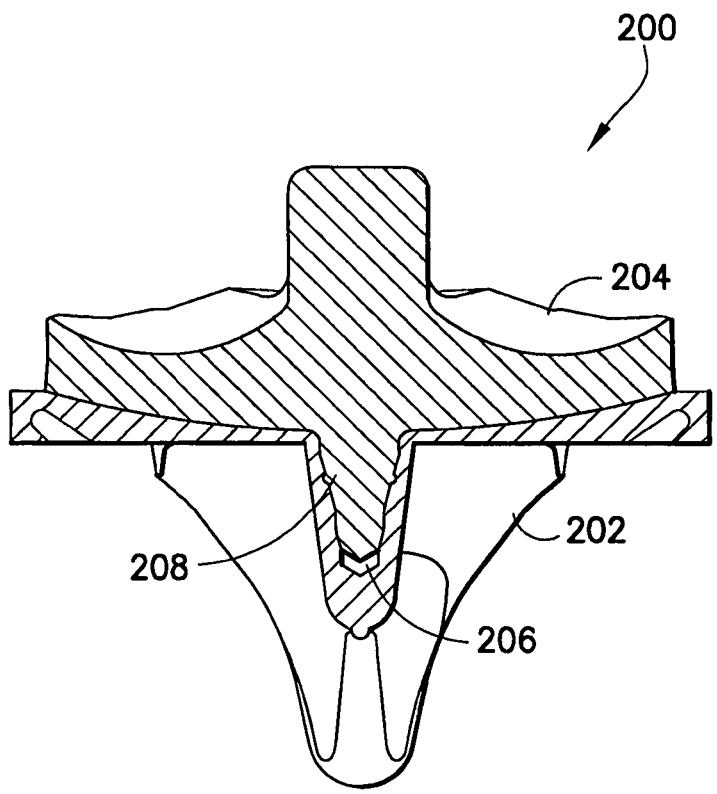
FIG. 2B shows a cross section taken along line H-H of FIG. 2A.
Figure 2C:
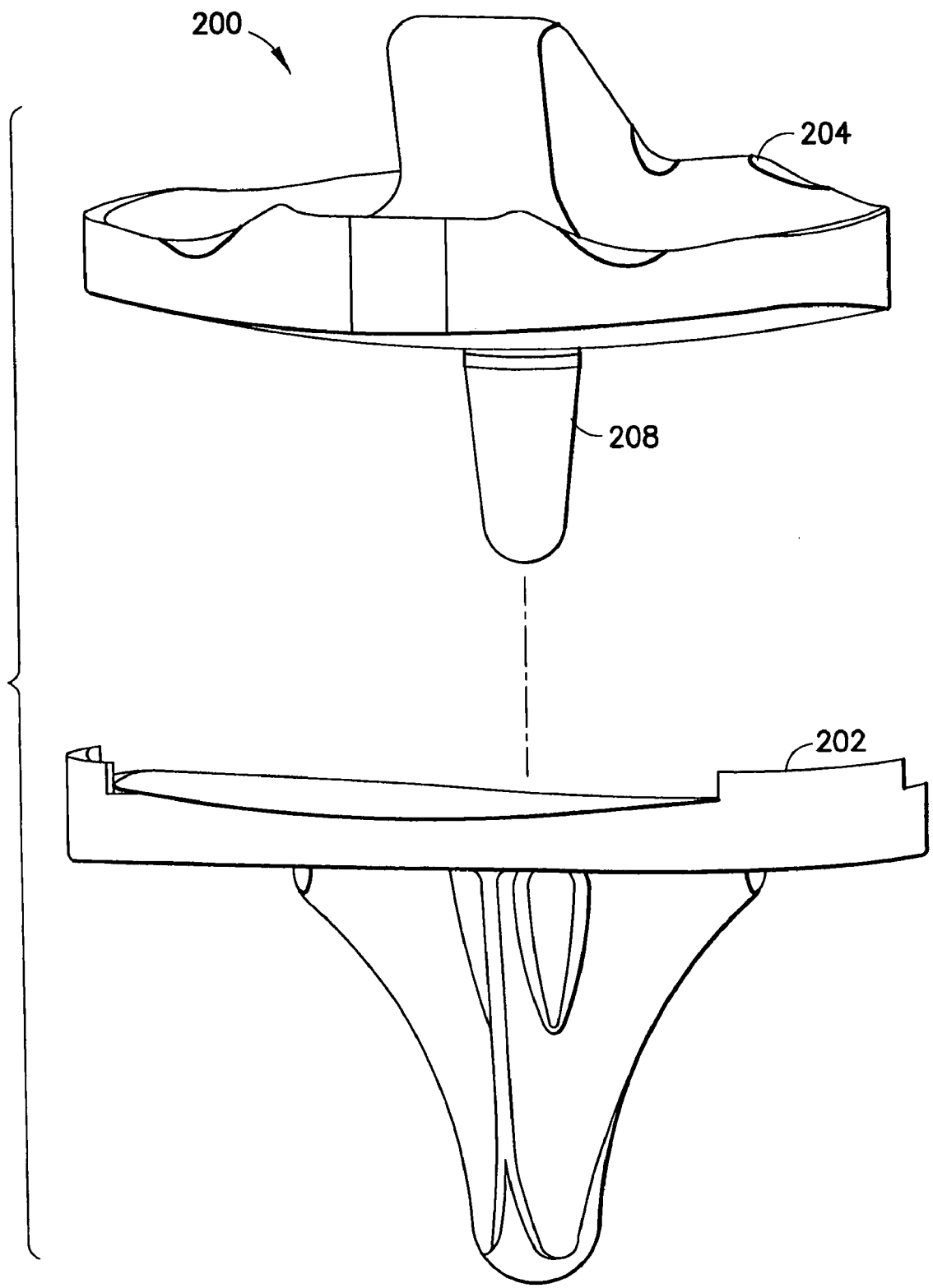
FIG. 2C shows a perspective view of the mobile bearing knee prosthesis of FIG. 2A.

Referring now to FIGS. 2A-2C, it is seen that the pivoting location may be placed where desired. For example (which example is intended to be illustrative and not restrictive) the pivoting location may be in the center (denoted by the dashed circle "A"), anterior (denoted by the dashed circle "B"), or posterior (denoted by the dashed circle "C") of Mobile Bearing Knee Prosthesis 200 (which may include Tibial Tray 202 and Tibial Insert 204). Of note, FIGS. 2A-2C show a mobile bearing knee prosthesis similar to that shown in FIGS. 1A-1E but without the Indentation/Raised Portion lift-off prevention mechanism. Of further note, it is believed that moving the pivoting location towards the posterior will tend to minimize moments on Post 208. In one example (which example is intended to be illustrative and not restrictive) rotational limits may be between about 50-53 degrees.

Figure 3:
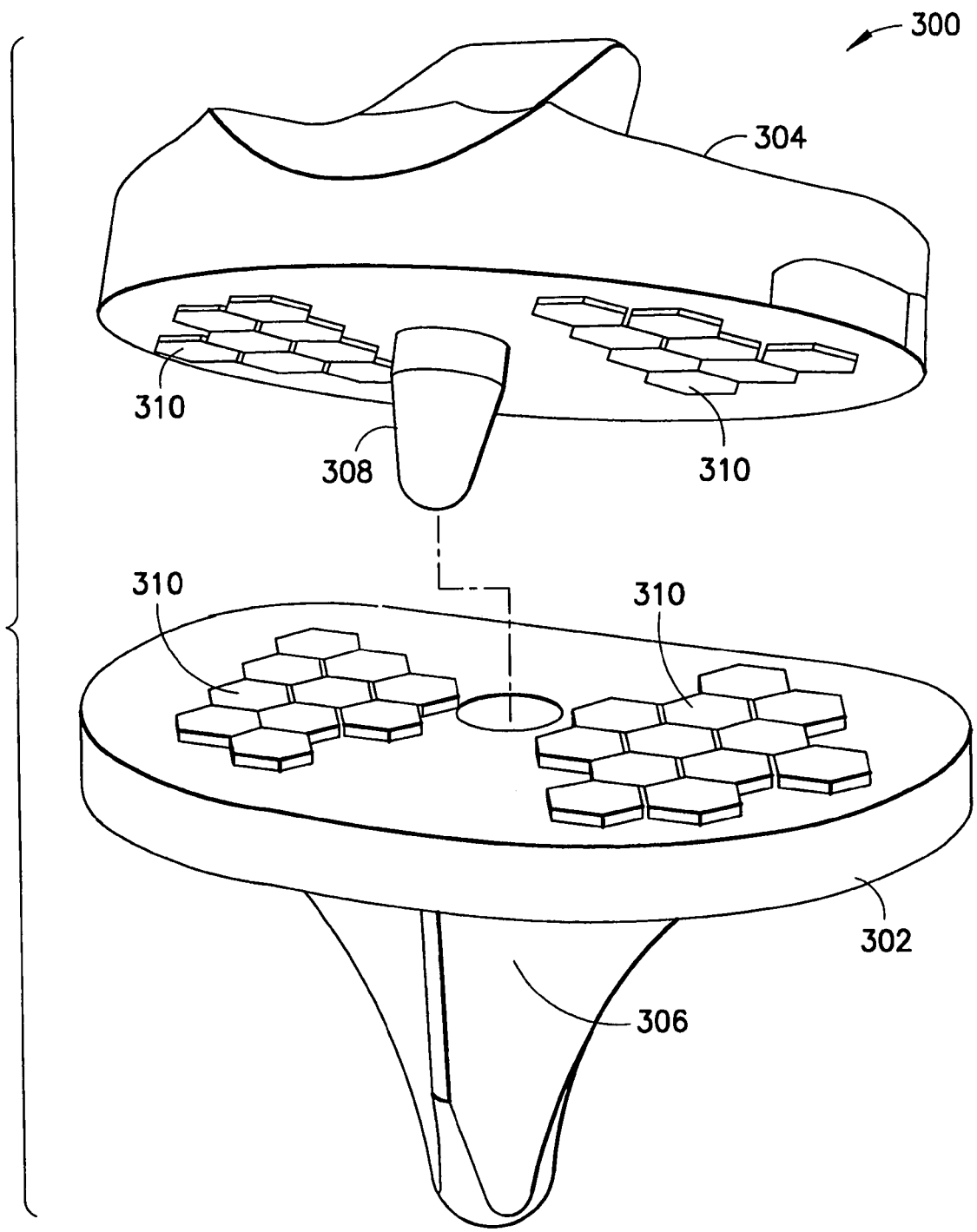
FIG. 3 shows a perspective view of a mobile bearing knee prosthesis according to another embodiment of the present invention.
Figure 4A:
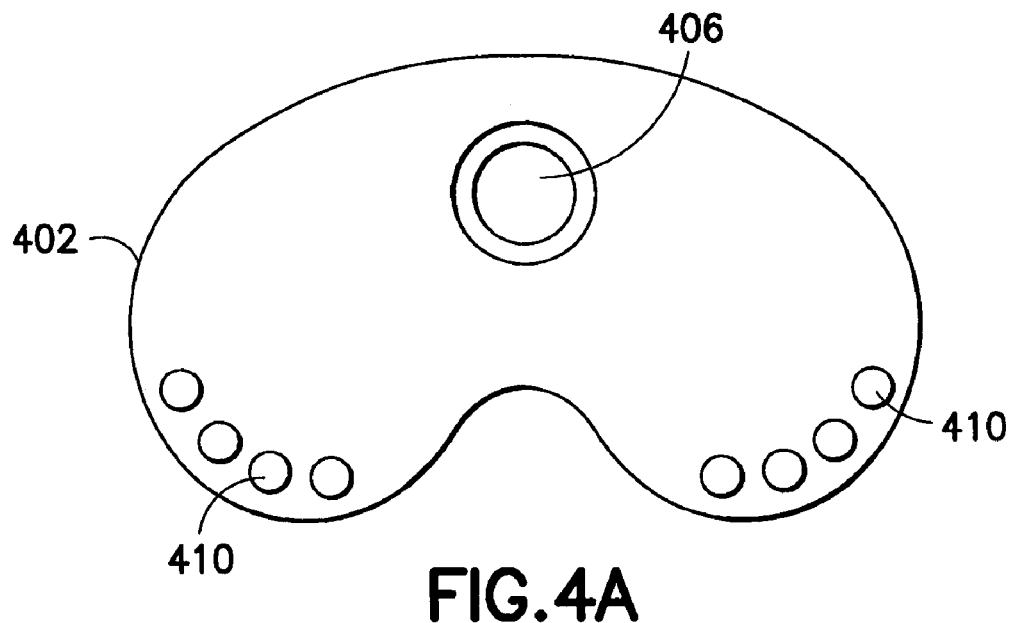
FIG. 4A shows a plan view of a tibial tray component of a mobile bearing knee prosthesis according to another embodiment of the present invention.
Figure 4B:
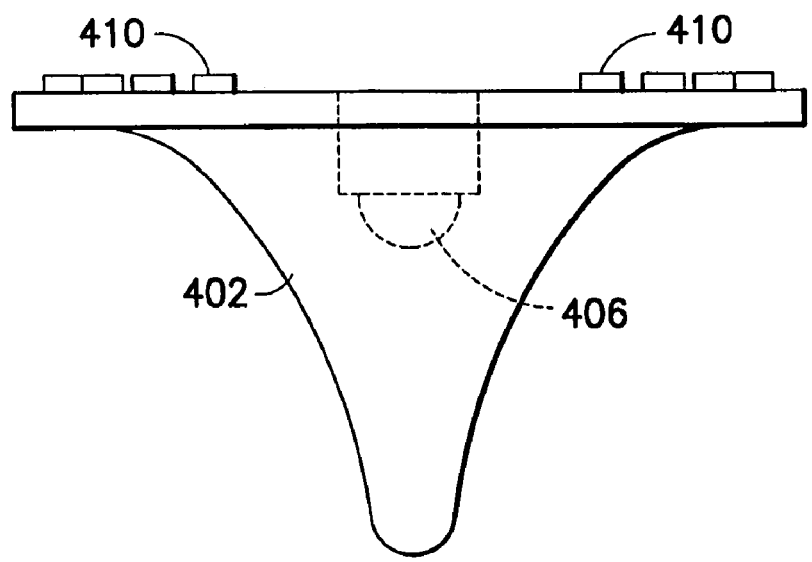
FIG. 4B shows a side view of the tibial tray component of FIG. 4A.
Figure 4C:
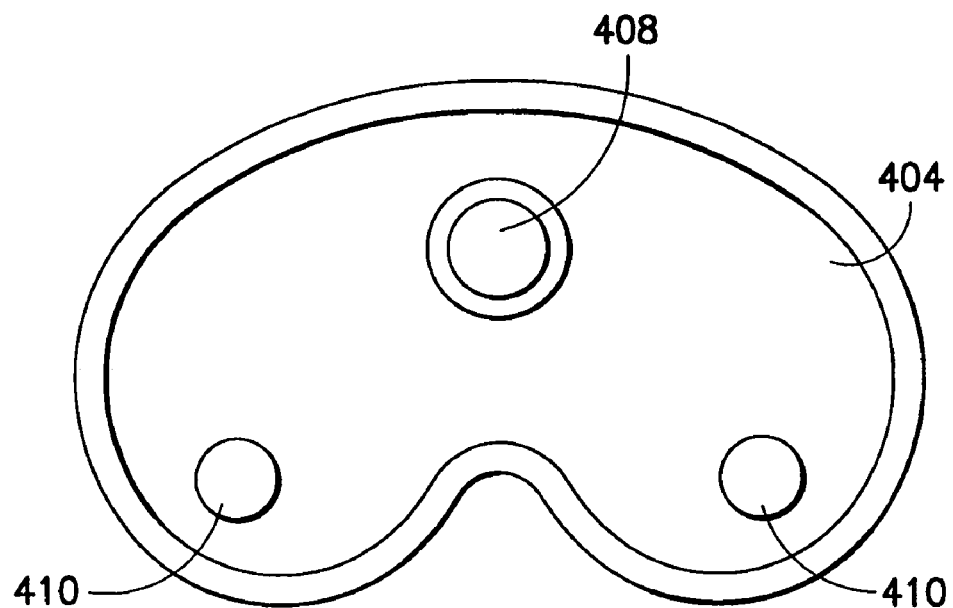
FIG. 4C shows a plan view of a tibial insert component of a mobile bearing knee prosthesis according to another embodiment of the present invention.
Figure 4D:
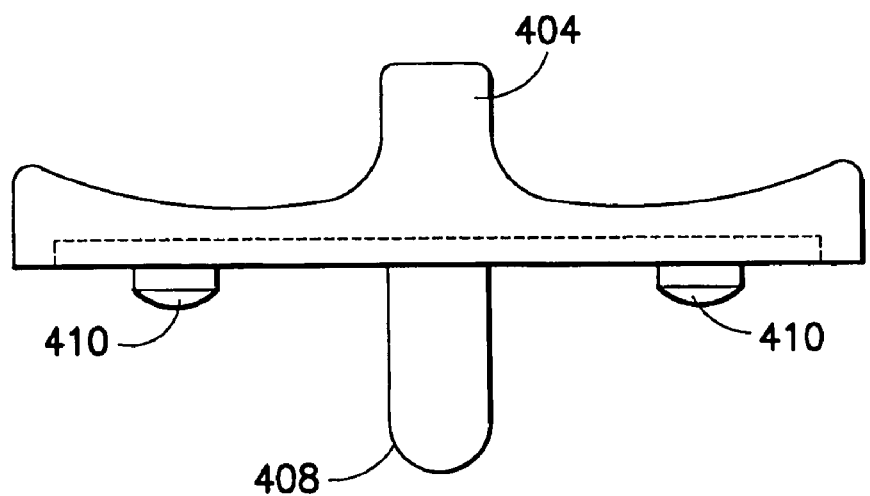
FIG. 4D shows a side view of the tibial insert component of FIG. 4C.

Referring now to FIG. 3, Mobile Bearing Knee Prosthesis 300 may include Tibial Tray 302, Tibial Insert 304 and Femoral Component (not shown) which interfaces with Tibial Insert 304. Mobile Bearing Knee Prosthesis 300 may include one or more diamond bearing surfaces 310 on an articulating surface of Tibial Tray 302, on an articulating surface of Tibial Insert 304, in Cavity 306 and/or on Post 308. In this regard, isolation of the articulating surface of Tibial Insert 304 (e.g., the polyethylene surface) from the articulating surface of Tibial Tray 302 with the highly wear-resistant diamond bearing surface(s) 310 helps avoid the problem of backside wear typically inherent in conventional mobile bearing knee prostheses.

Referring now to FIGS. 4A-4D, a mobile bearing knee prosthesis may include Tibial Tray 402, Tibial Insert 404 and Femoral Component (not shown) which interfaces with Tibial Insert 404. The mobile bearing knee prosthesis may include diamond bearing surface(s) 410 on an articulating surface of Tibial Tray 402, on an articulating surface of Tibial Insert 404, in Cavity 406 and/or on Post 408. In one example (which example is intended to be illustrative and not restrictive) 3-point contact associated with the diamond bearing surface(s) 410 may establish a plane. In another example (which example is intended to be illustrative and not restrictive) one or more of the diamond bearing surface(s) 410 (e.g., the diamond bearing surface(s) 410 on Tibial Insert 404) may be spherical or hemi-spherical in shape (e.g., to avoid or attenuate edge loading). In another example (which example is intended to be illustrative and not restrictive) one or more of the diamond bearing surface(s) 410 may be press-fit.

Figure 5A:
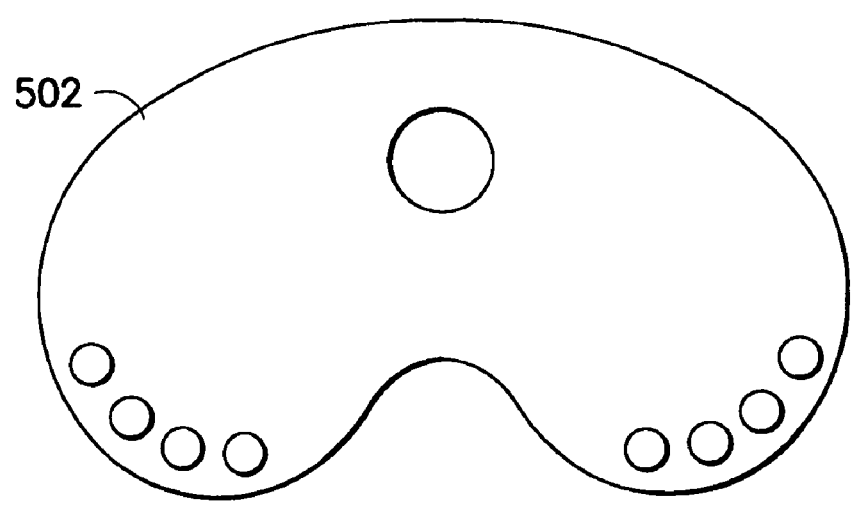
FIG. 5A shows a plan view of a tibial tray component of a mobile bearing knee prosthesis according to another embodiment of the present invention.
Figure 5B:
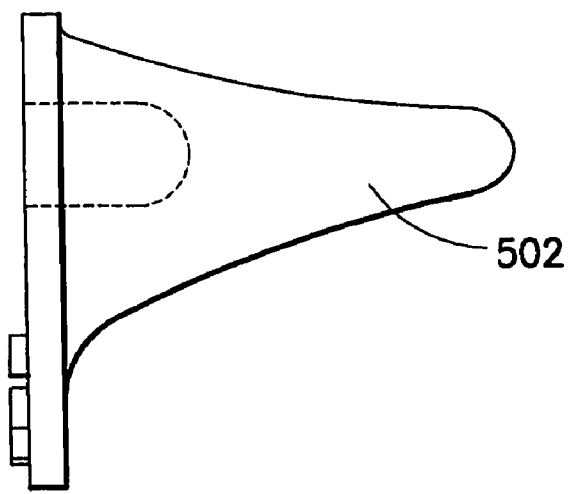
FIG. 5B shows a side view of the tibial tray component of FIG. 5A.

In another example a rotary stop mechanism may be provided to help ensure that the diamond bearing surface(s) (e.g., the posterior, medial and lateral diamond bearing surface(s)) remain engaged at all times. In another example (which example is intended to be illustrative and not restrictive) this rotary stop mechanism may be diamond against diamond. In this regard, see FIGS. 5A and 5B, where the most anterior diamond bearing of Tibial Tray 502, for example, is elevated (to cause the medial and lateral diamond bearings on the underside of the Tibial Insert (not shown) to abut and constrain rotary motion).

Figure 6A:
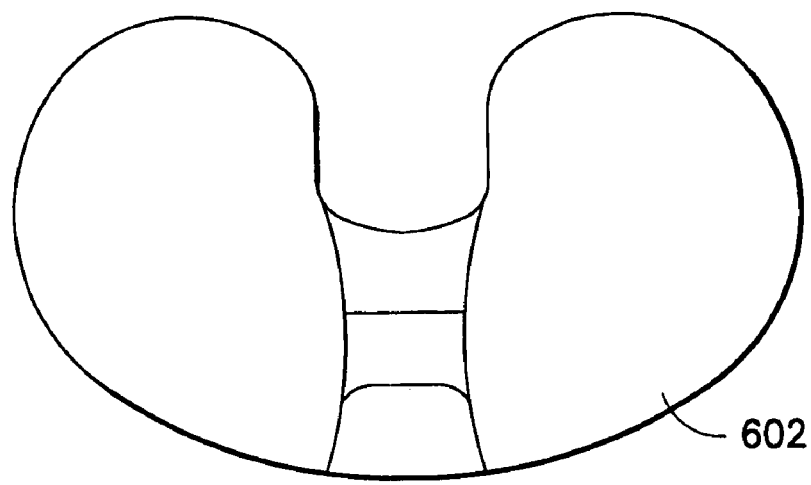
FIG. 6A shows a plan view of a tibial tray component of a mobile bearing knee prosthesis according to another embodiment of the present invention.
Figure 6B:
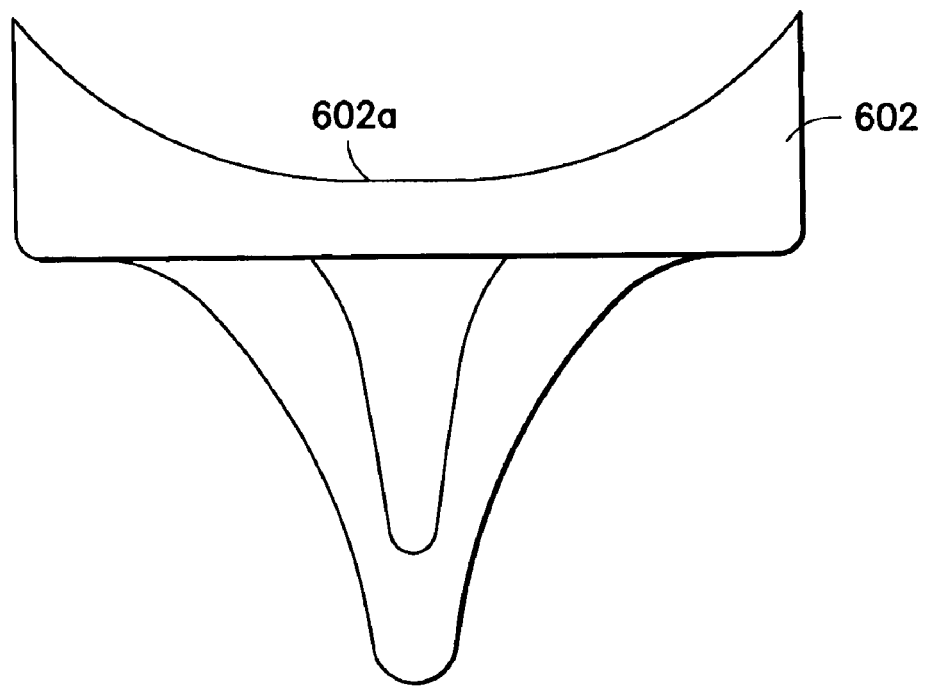
FIG. 6B shows a side view of the tibial tray component of FIG. 6A.

Referring now to FIGS. 6A and 6B, a Tibial Tray 602 for a mobile bearing knee prosthesis may include a large diameter surface, such as a spherical surface (a Tibial Insert (not shown) may have a mating large diameter surface, such as a spherical surface, on a backside thereof). The Tibial Tray 602 may include Plane Surface 602a (which Plane Surface 602a is essentially flat). In one example (which example is intended to be illustrative and not restrictive) Plane Surface 602a may be a polyethylene component (e.g., a molded "puck"). In a further example (which example is intended to be illustrative and not restrictive) the areas designated "A" in FIG. 6A may maintain a high contact area.

Figure 7A:
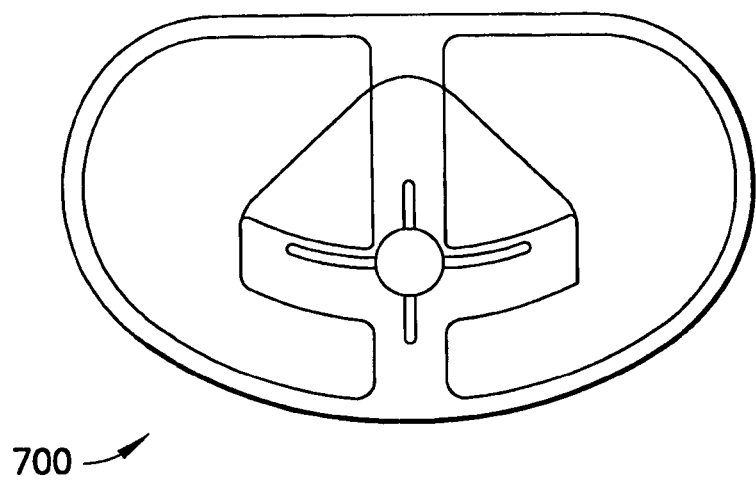
FIG. 7A shows a plan view of a mobile bearing knee prosthesis according to another embodiment of the present invention.
Figure 7B:
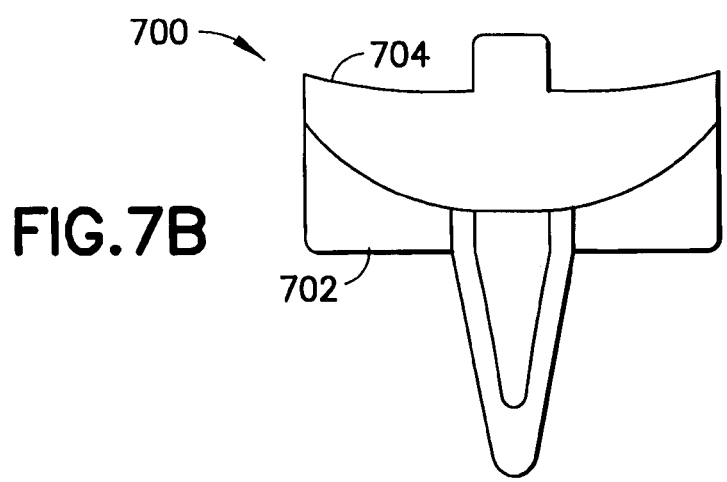
FIG. 7B shows a cross section of the mobile bearing knee prosthesis of FIG. 7A.
Figure 7C:
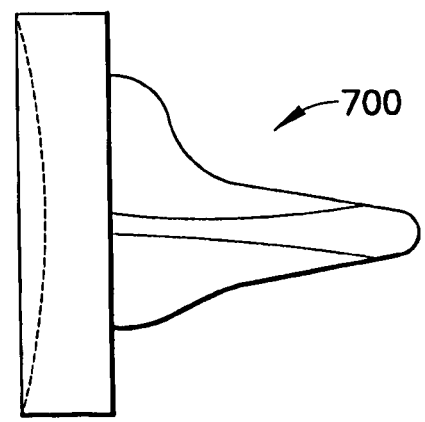
FIG. 7C shows a side view of the tibial tray of the mobile bearing knee prosthesis of FIG. 7A.

Referring now to FIGS. 7A-7C, Mobile Bearing Knee Prosthesis 700 may include Tibial Tray 702, Tibial Insert 704 and Femoral Component (not shown) which interfaces with Tibial Insert 704. In one example (which example is intended to be illustrative and not restrictive) Tibial Tray 702 may have a concave articulating surface and Tibial Insert 704 may have a convex articulating surface. The aforementioned articulating surfaces may comprise a large radius sphere (e.g., for backside articulation of a rotating/mobile prosthesis).

In another example (which example is intended to be illustrative and not restrictive) there may be a tighter clearance at the area designated "A" in FIG. 7B then there is at the area designated "B" in FIG. 7B.

Figure 8A:
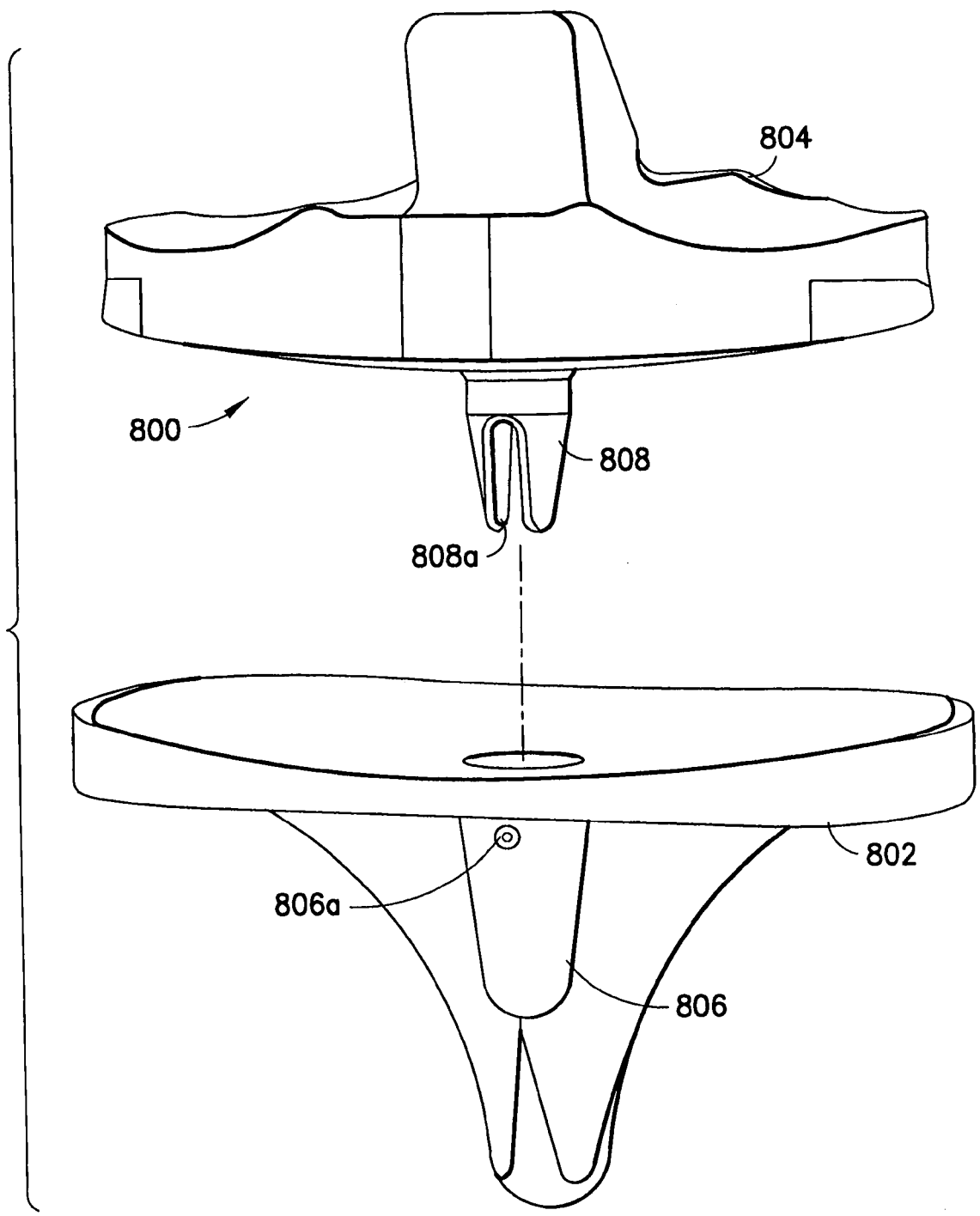
FIG. 8A shows a perspective view of a mobile bearing knee prosthesis according to another embodiment of the present invention.
Figure 8B:
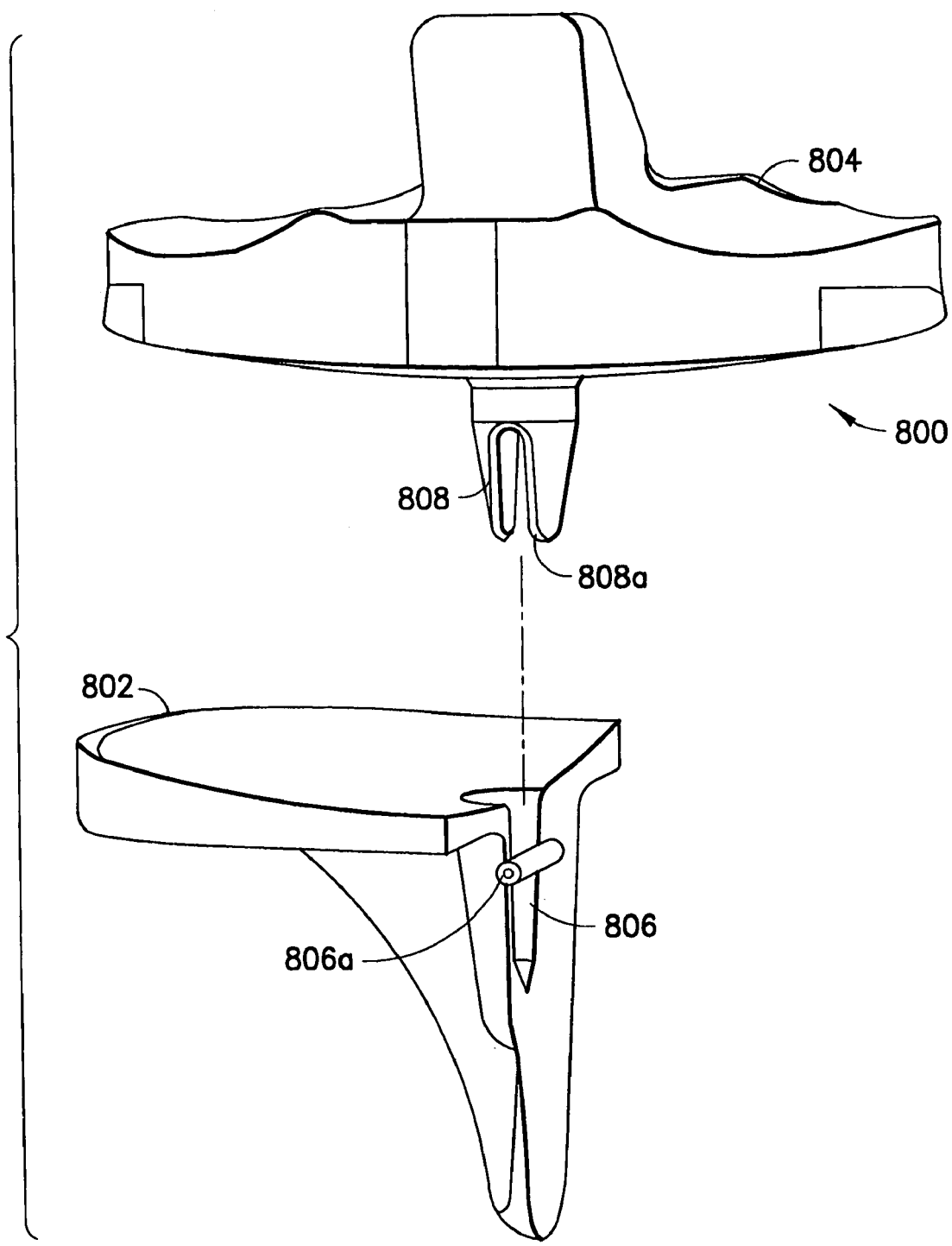
FIG. 8B shows a perspective view (partially cut-away) of the mobile bearing knee prosthesis of FIG. 8A.
Figure 8C:
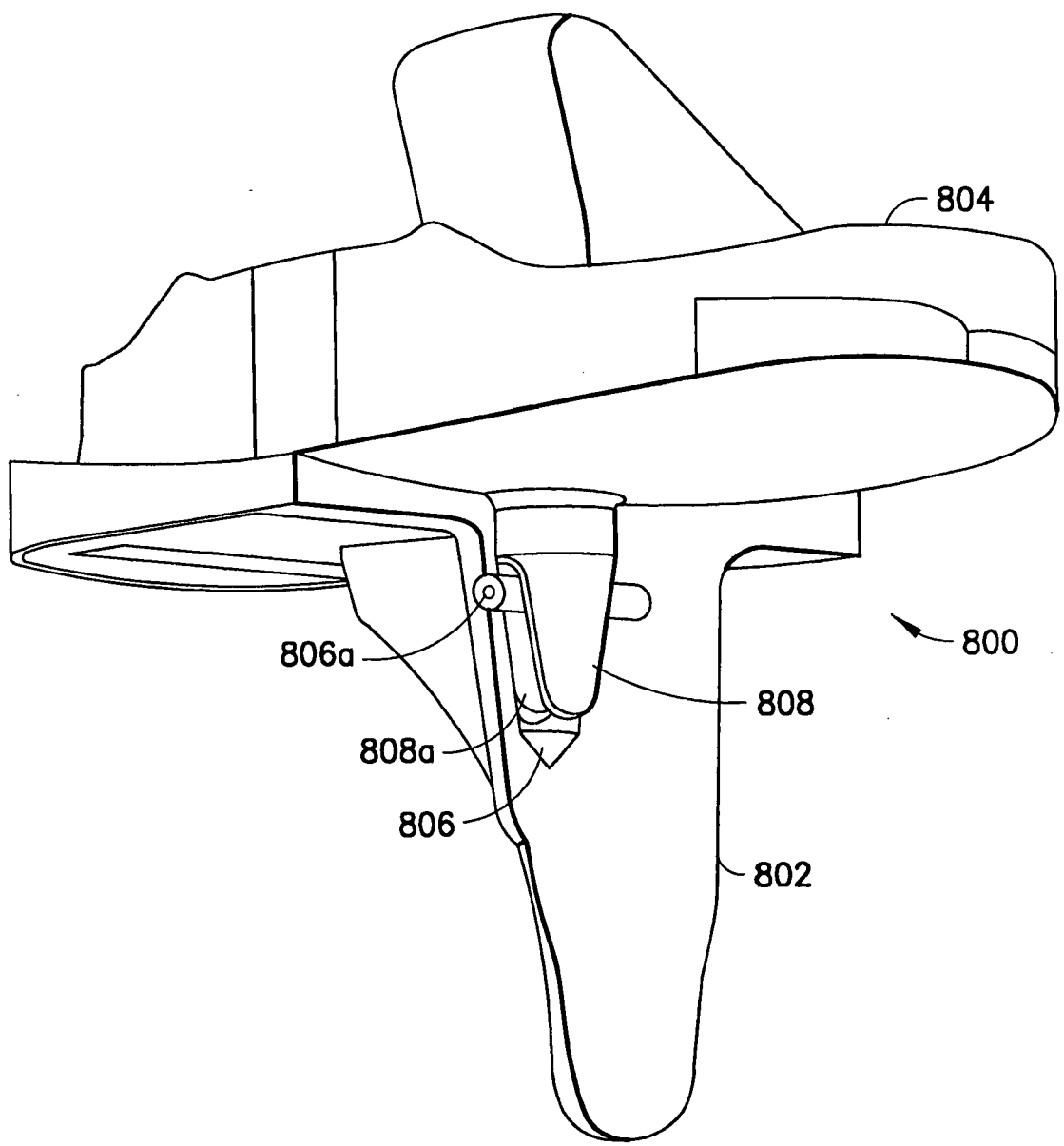
FIG. 8C shows a perspective view (partially cut-away) of the mobile bearing knee prosthesis of FIG. 8A.

Referring now to FIGS. 8A-8C an embodiment adapted to aid in rotational constraint and/or control is shown.

More particularly, Mobile Bearing Knee Prosthesis 800 may include Tibial Tray 802, Tibial Insert 804 and Femoral Component (not shown) which interfaces with Tibial Insert 804. Mobile Bearing Knee Prosthesis 800 may have a pivoting location defined by Cavity 806 that mates with Post 808. Further, Cross-pin 806A may mate with Groove 808a such that during rotation of Tibial Insert 804 the Cross-pin 806a acts as a rotational stop and Post 808 acts as a spring (i.e., a torsion spring to give resistance to rotation).

In one example (which example is intended to be illustrative and not restrictive) the diameter of Cross-pin 806a and/or the size of Groove 808a may be varied to provide different levels of rotational constraint and/or control.

In another example (which example is intended to be illustrative and not restrictive) the Cross-pin 806a may be installed prior to implantation of Tibial Tray 802 (whereby Groove 808a allows Tibial Insert 804 to be installed with Tibial Tray 802 in place in the body (e.g., cemented in place).

Referring now to FIGS. 9A-9D and 10A-10E various additional embodiments adapted to aid in rotational constraint and/or control and/or to help prevent tibial insert lift-off are shown.

Figure 9A:
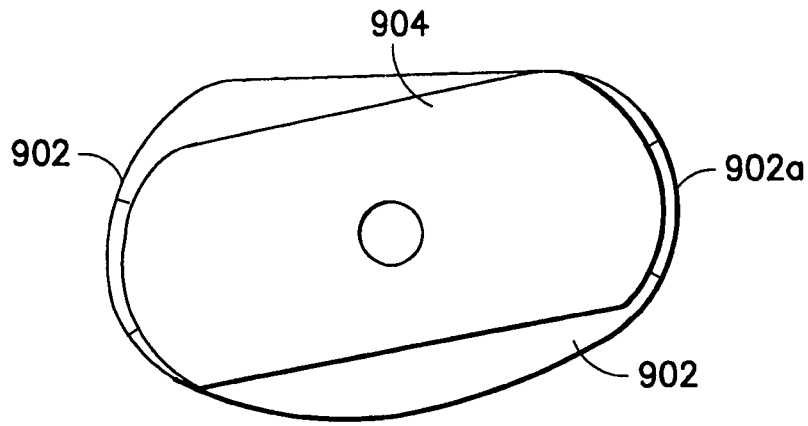
FIG. 9A shows a top plan view of a mobile bearing knee prosthesis according to another embodiment of the present invention (wherein a tibial insert is shown rotated and locked in place on a tibial tray)
Figure 9B:
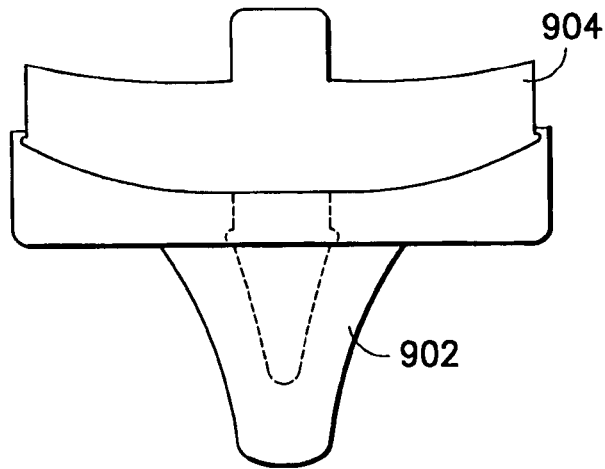
FIG. 9B shows a cross section of the mobile bearing knee prosthesis of FIG. 9A.
Figure 9C:
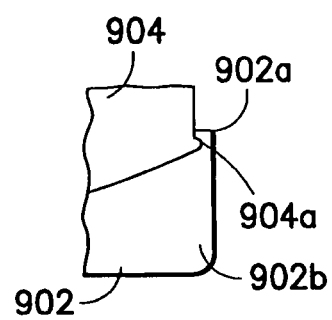
FIG. 9C shows certain detail associated with the mobile bearing knee prosthesis of FIG. 9A.
Figure 9D:
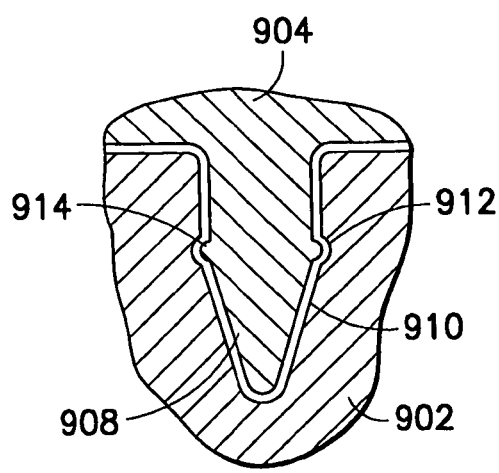
FIG. 9D shows certain detail associated with the mobile bearing knee prosthesis of FIG. 9A.

More particularly, as seen in FIGS. 9A-9C, when Tibial Insert 904 is rotated it contacts Rotation Limiting Tabs 902a of Tibial Tray 902 (to thereby wedge Tibial Insert 904 in place and inhibit further rotation).

Further, each Rotation Limiting Tab 902a may include Undercut 902b to help prevent lift-off when extremes of rotation have been reached (In this regard, Tibial Insert 904 may include one or more Lips 904a for engaging Rotational Limiting Tabs 902a and/or Undercuts 902b).

Further still, Tibial Insert 904 may include Post 908 which resides in Cavity 910 in Tibial Tray 902, whereby Cavity 910 includes Indentation 912 for receiving Raised Portion 914 of Post 908. Indentation 912 and Raised Portion 914 may thus cooperate to help prevent lift-off of Tibial Insert 904. In one example (which example is intended to be illustrative and not restrictive) the running clearance between Post 908 and Cavity 910 may be between about 0.005 and 0.010 inches.

Figure 10A:
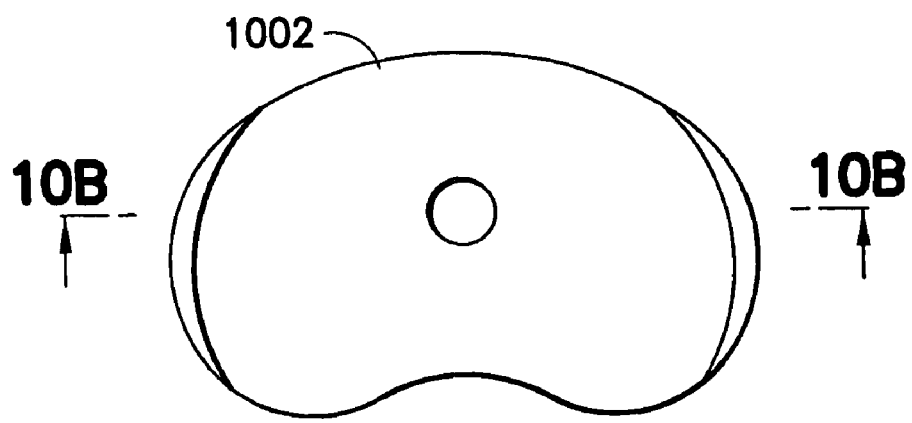
FIG. 10A shows a plan view of a tibial tray according to another embodiment of the present invention.
Figure 10B:
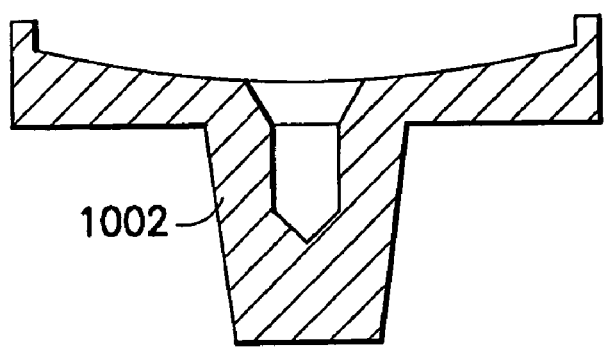
FIG. 10B shows a cross section of the tibial tray of FIG. 10A.
Figure 10C:
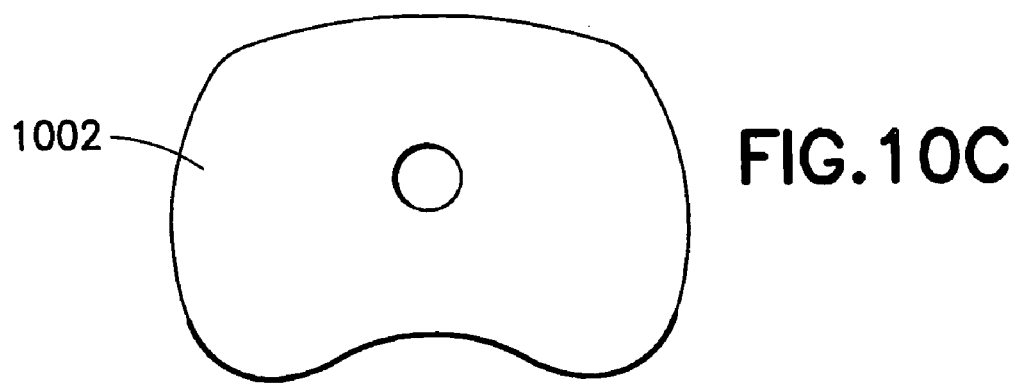
FIG. 10C shows a plan view of a tibial insert for use with the tibial tray of FIG. 10A.

Further still, FIGS. 10A and 10B show a distance "A" inside an outer wall section of Tibial Tray 1002; FIG. 10C shows distances $B_1$, $B_2$ and C associated with Tibial Insert 1004 (wherein distance $B_1$ and $B_2$ are greater than distance A and distance C is less than distance A); and FIG. 10D shows contact points between Tibial Tray 1002 and Tibial Insert 1004 when Tibial Insert 1004 is rotated (in the clockwise direction in this example).

Figure 10D:
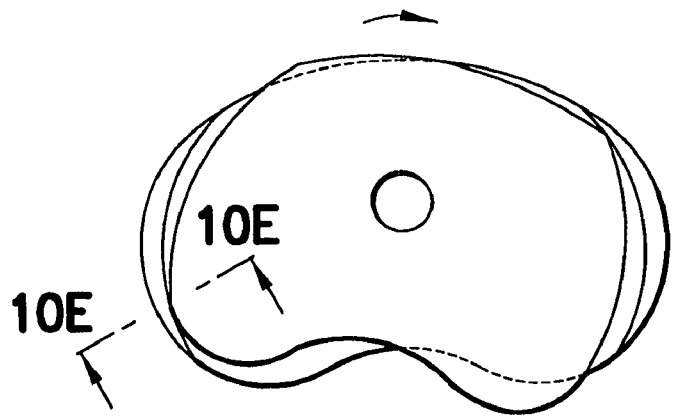
FIG. 10D shows a plan view of the tibial tray and tibial insert of FIGS. 10A-10C.
Figure 10E:
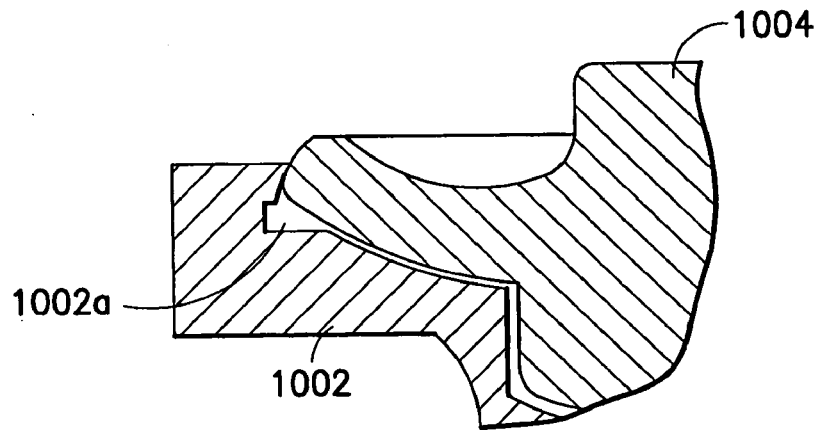
FIG. 10E shows certain detail taken along line B-B of FIG. 10D.
Figure 10F:
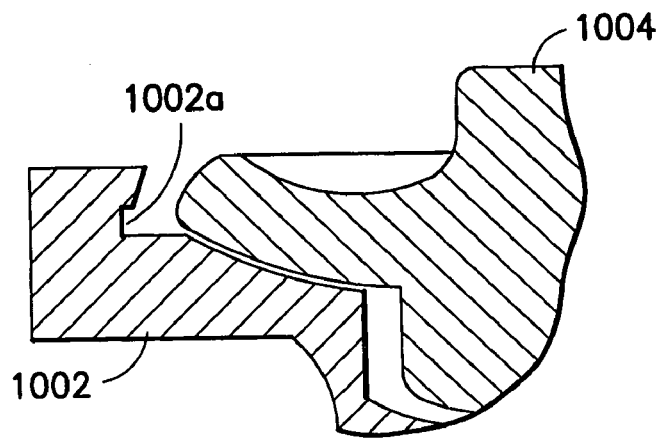
FIG. 10F shows certain detail taken along line B-B of FIG. 10D.

Further still, FIG. 10E shows detail of the interference between Tibial Tray 1002 and Tibial Insert 1004 at a contact point of FIG. 10D and FIG. 10F shows that there is no interference at the contact point of FIG. 10E when the Tibial Insert 1004 is not rotated past a certain point (e.g., at a "neutral position"). Of note, FIGS. 10E and 10F also show Recess 1002a, which may be used for example for poly flow and/or to aid in preventing lift-off.

Figure 11:
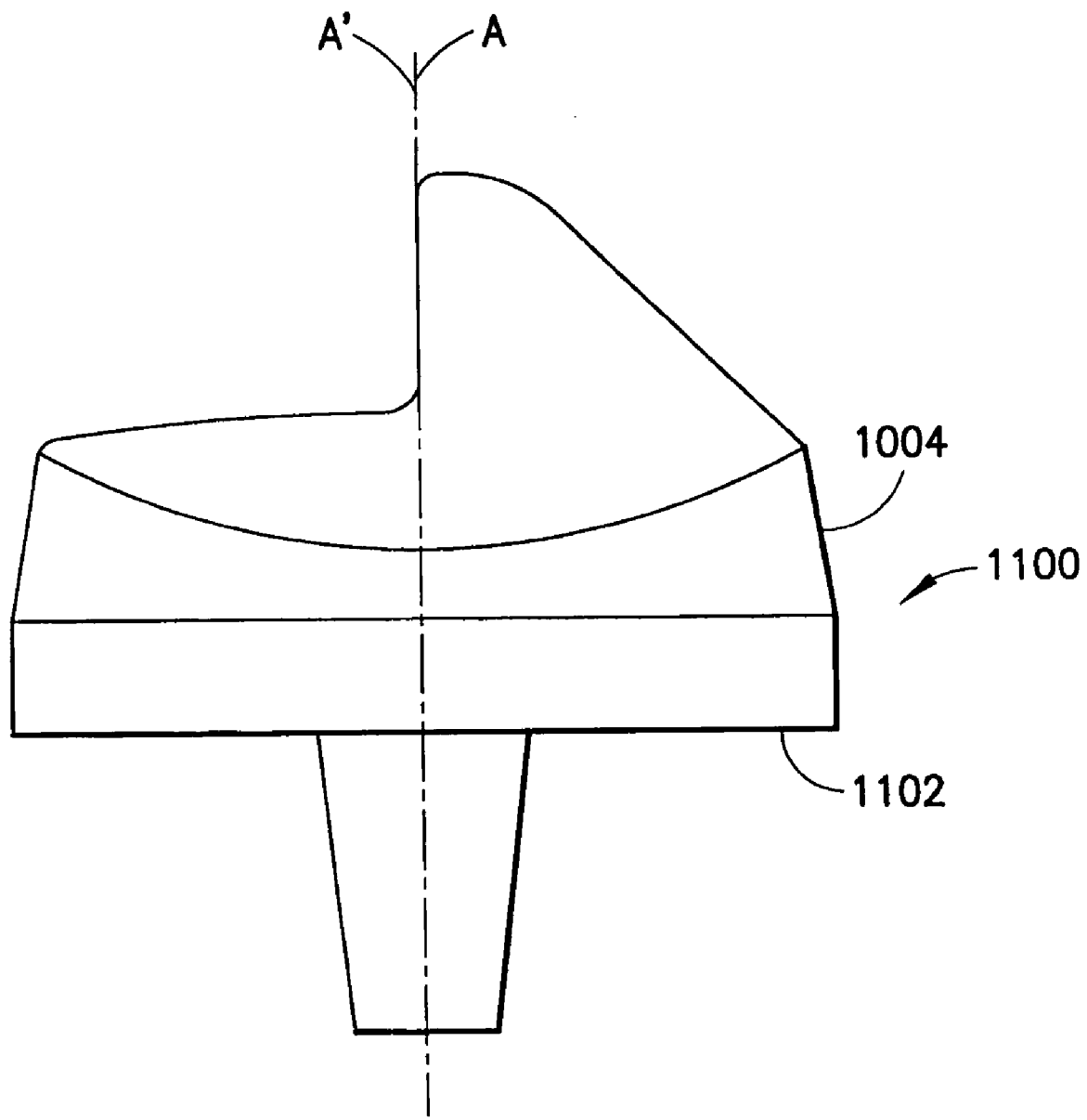
FIG. 11 shows a side view of a mobile bearing knee prosthesis according to another embodiment of the present invention.

Referring now to FIG. 11, it is seen that Mobile Bearing Knee 1100 according to an embodiment of the present invention may include Tibial Tray 1102 and Tibial Insert 1104, wherein the rotational axis A of Mobile Bearing Knee 1100 may be placed in-line with the natural axis A' of the knee.

Figure 12A:
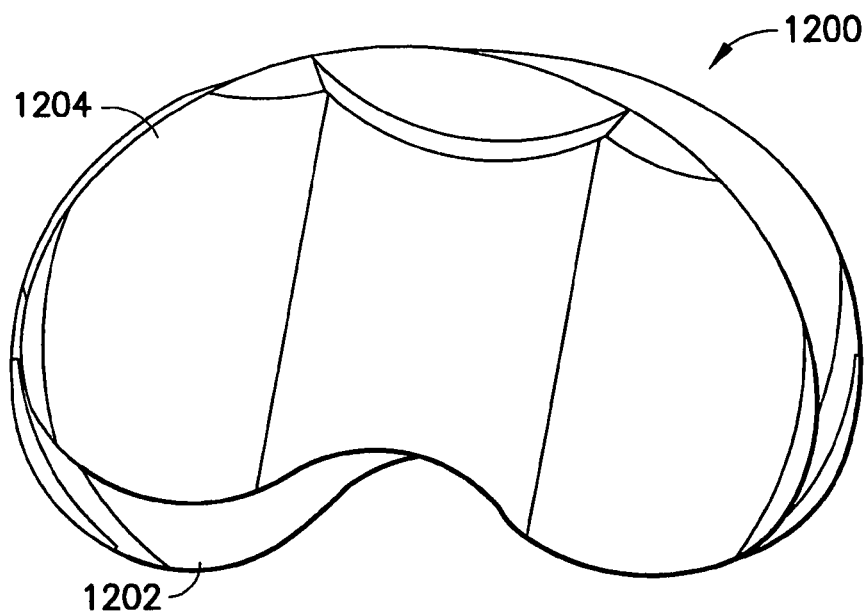
FIG. 12A shows a plan view of a mobile bearing knee prosthesis according to another embodiment of the present invention.
Figure 12B:
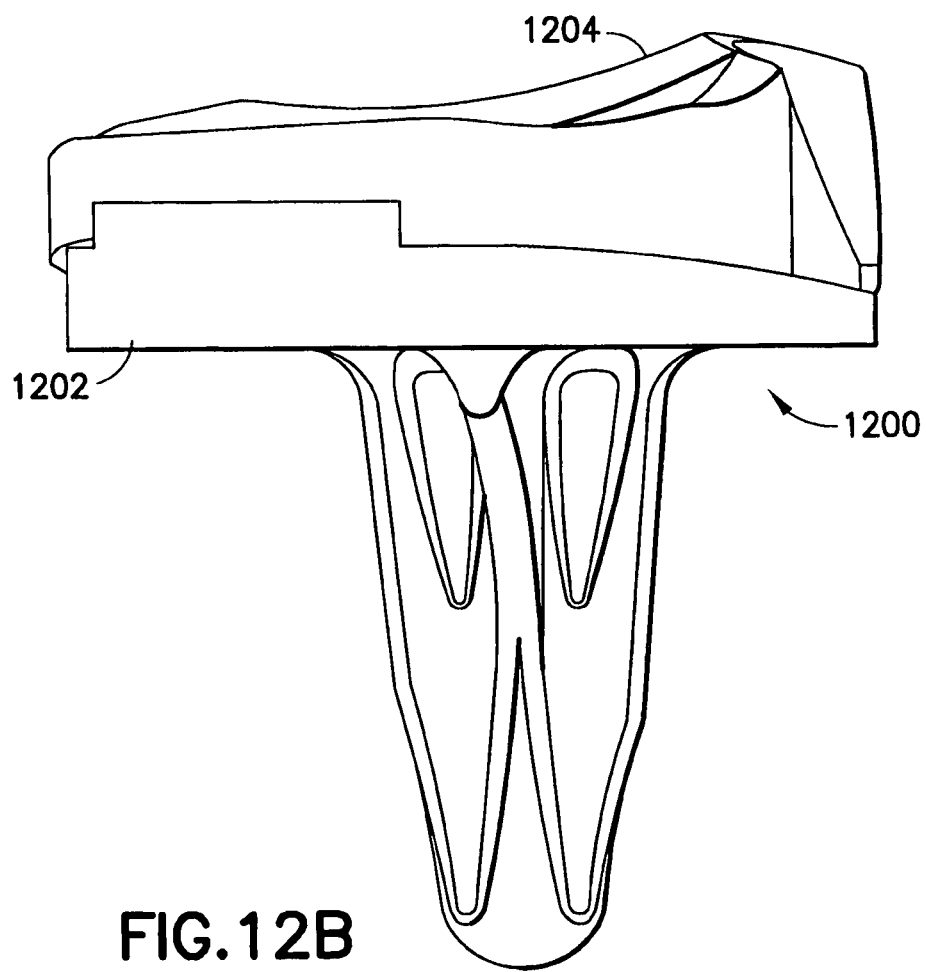
FIG. 12B shows a side view of the mobile bearing knee prosthesis of FIG. 12A.
Figure 13A:
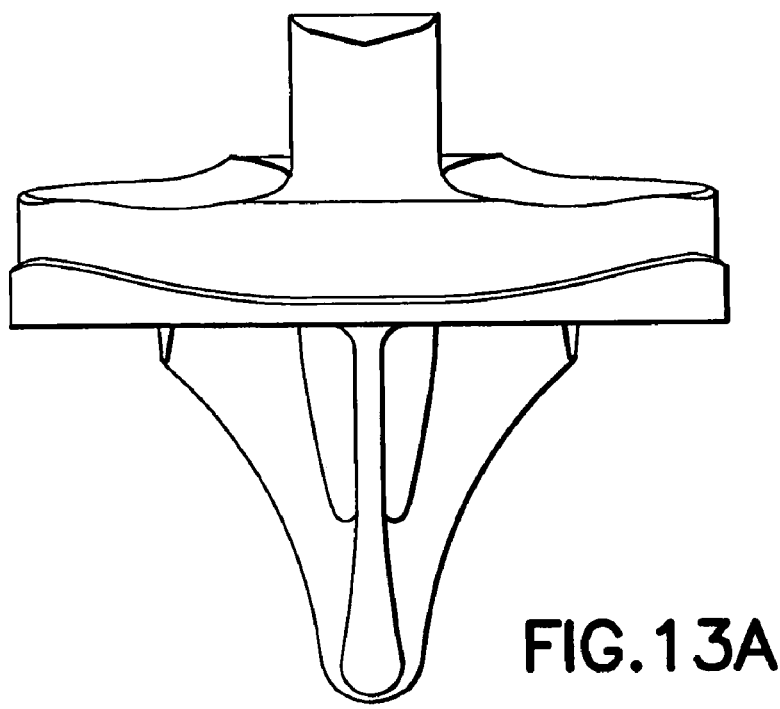
FIG. 13A shows an elevation view of a mobile bearing knee according to another embodiment of the present invention (in this view a tibial insert and a tibial tray are engaged and a uniform curvature between mating parts is seen)
Figure 13B:
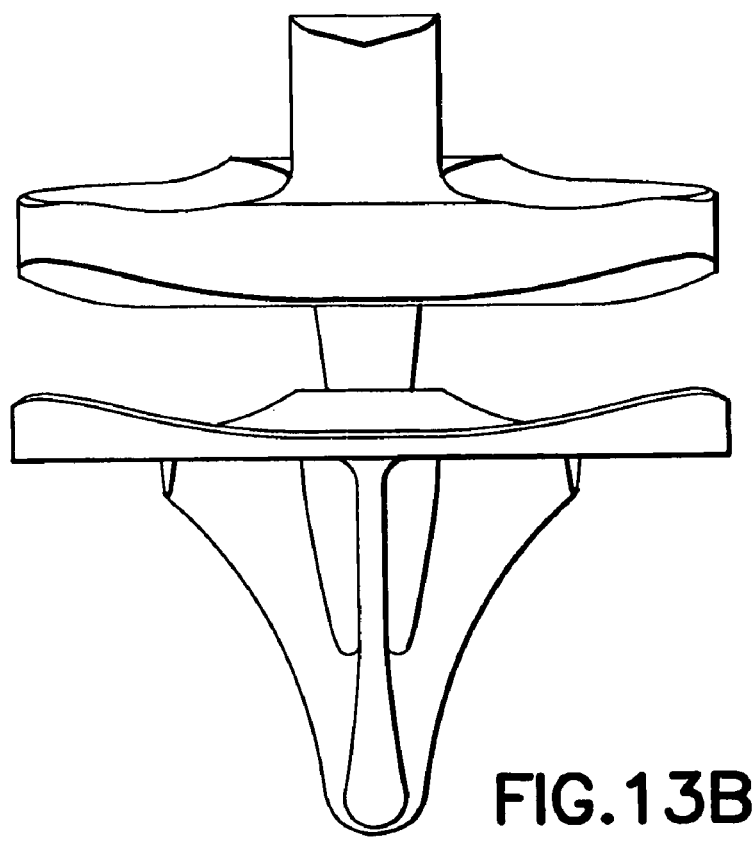
FIG. 13B shows an elevation view of a mobile bearing knee according to the embodiment of FIG. 13A (in this view a tibial insert and a tibial tray are partially engaged and a uniform curvature between mating parts is seen)
Figure 13C:
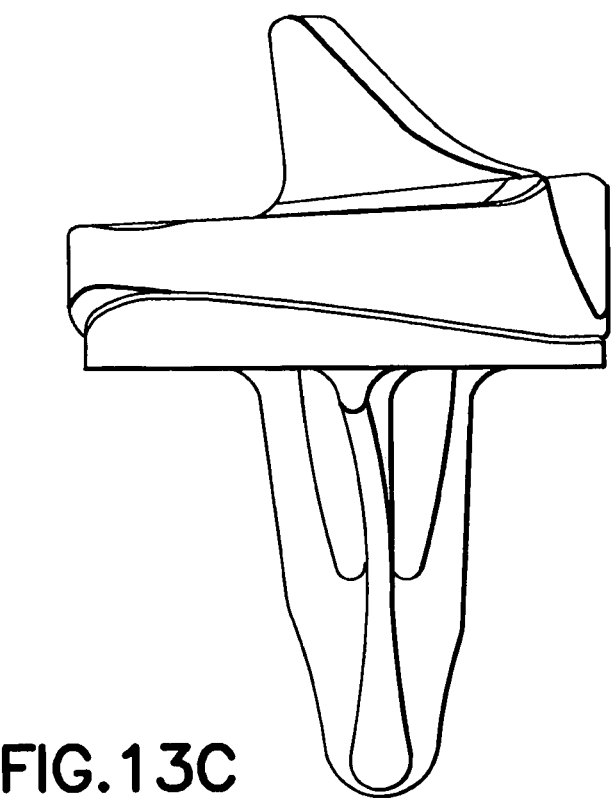
FIG. 13C shows a side elevation view of a mobile bearing knee according to the embodiment of FIG. 13A (in this view a tibial insert and a tibial tray are engaged and a uniform curvature between mating parts is seen)
Figure 13D:
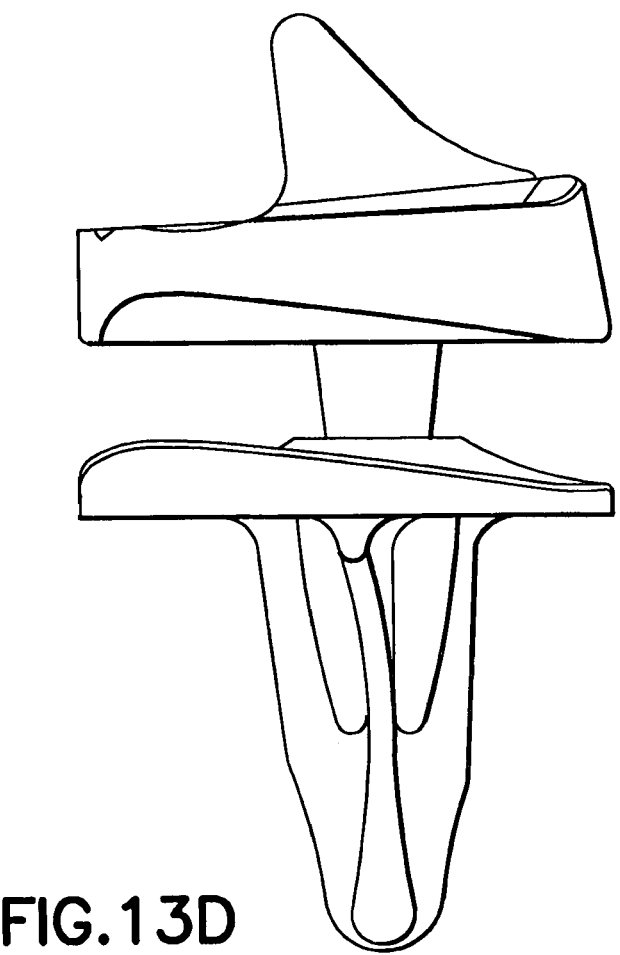
FIG. 13D shows a side elevation view of a mobile bearing knee according to the embodiment of FIG. 13A (in this view a tibial insert and a tibial tray are partially engaged and a uniform curvature between mating parts is seen)
Figure 13E:
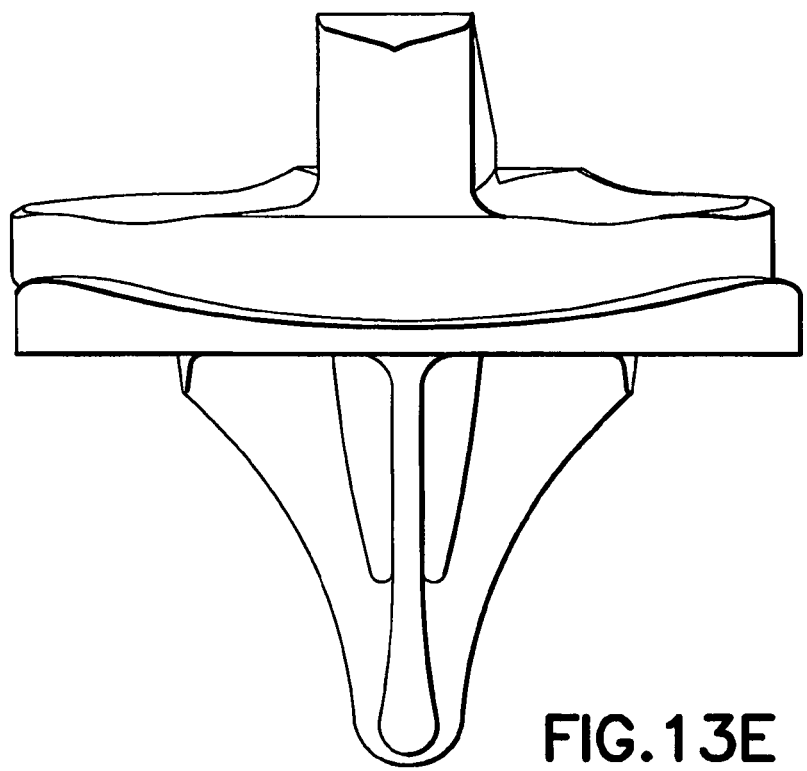
FIG. 13E shows another elevation view of a mobile bearing knee according to the embodiment of FIG. 13A (in this view a tibial insert and a tibial tray are engaged, the tibial insert is rotated 10° relative to the tibial tray, and a uniform curvature between mating parts is seen)
Figure 13F:
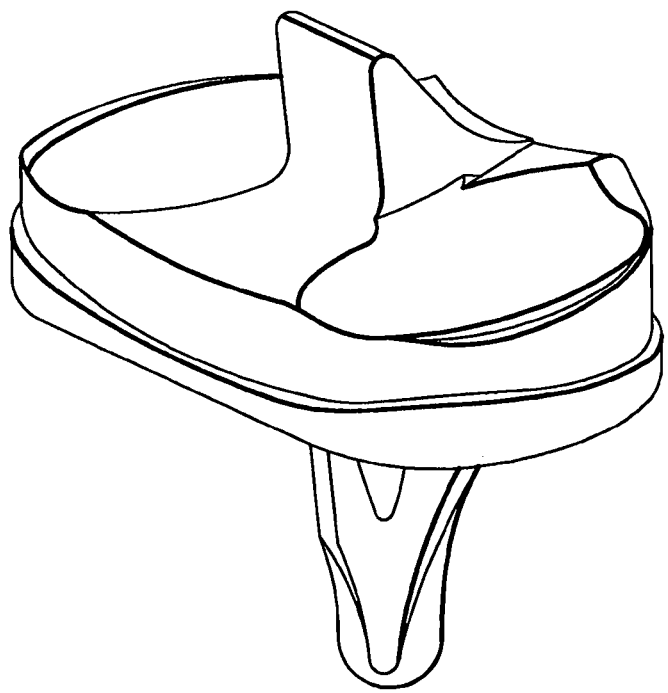
FIG. 13F shows a perspective view of a mobile bearing knee according to the embodiment of FIG. 13A (wherein a tibial insert and a tibial tray are engaged, and a uniform curvature between mating parts is seen)
Figure 14A:
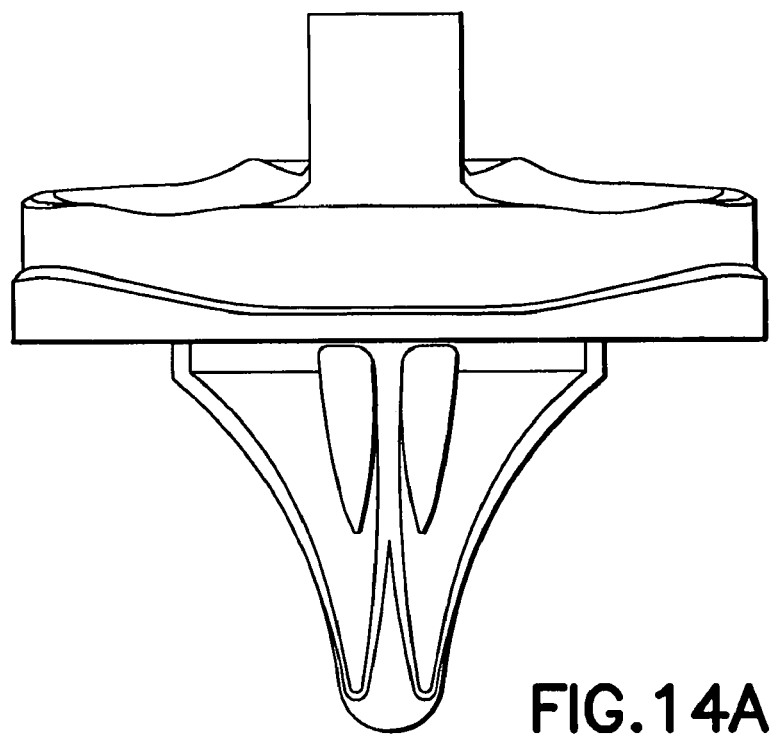
FIG. 14A shows another elevation view of a mobile bearing knee according to the embodiment of FIG. 13A (wherein the Figure includes a cross-sectional line indicator through the center of the mobile bearing knee)
Figure 14B:
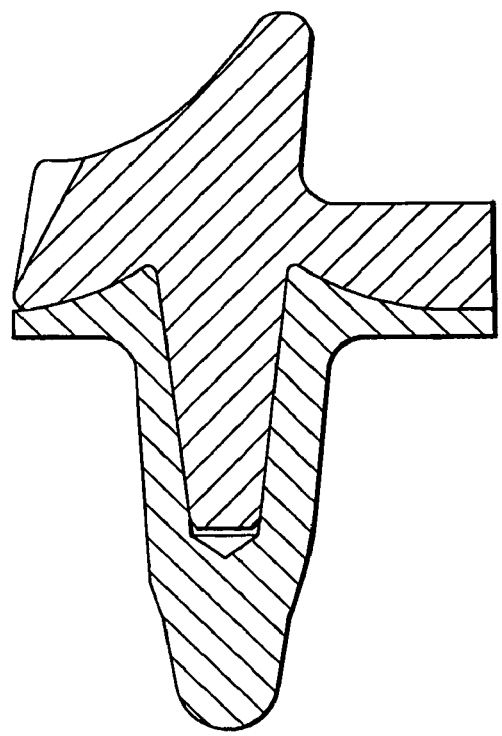
FIG. 14B shows a cross-section along the cross-sectional line indicator of FIG. 14A (wherein the relationship of the "wave" geometry to an axial post on the tibial insert is seen)
Figure 14C:
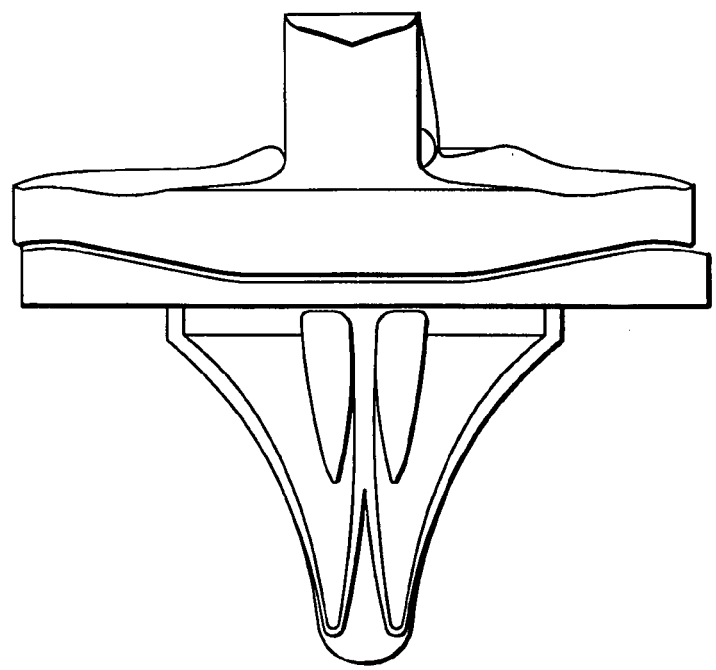
FIG. 14C shows another elevation view of a mobile bearing knee according to the embodiment of FIG. 13A (wherein the Figure includes a cross-sectional line indicator through the center of the mobile bearing knee and the tibial insert is rotated 10° relative to the tibial tray)
Figure 14D:
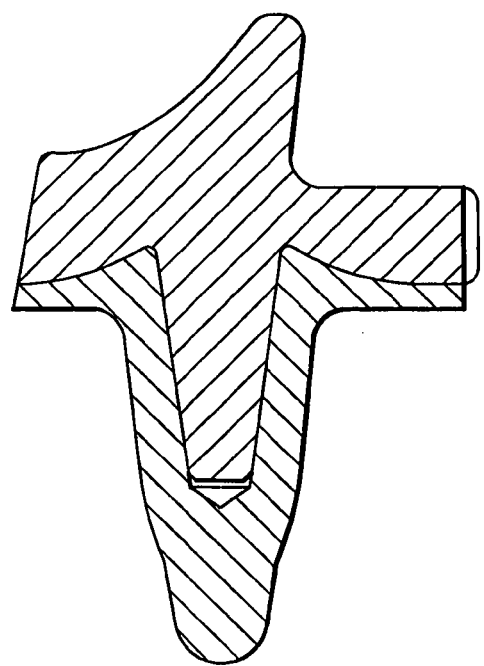
FIG. 14D shows a cross-section along the cross-sectional line indicator of FIG. 14C (wherein the relationship of the "wave" geometry to an axial post on the tibial insert is seen and the tibial insert is rotated 10° relative to the tibial tray)
Figure 15C:
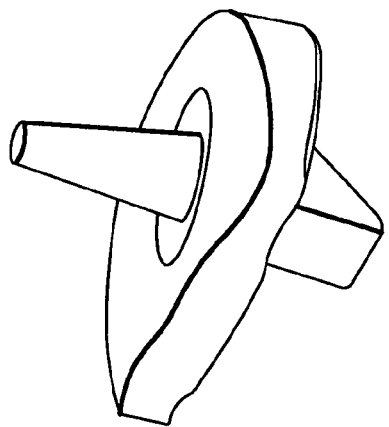
FIGS. 15A-15C show perspective views (at various angles) of the inferior surface of a tibial insert of a mobile bearing knee prosthesis according to an embodiment of the present invention.
Figure 15B:
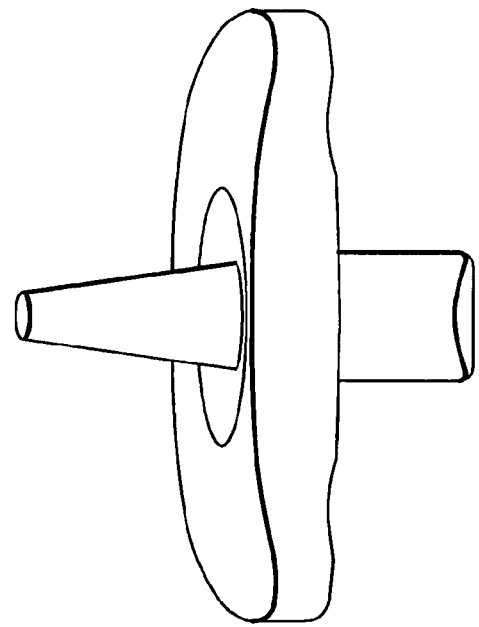
Figure 15A:
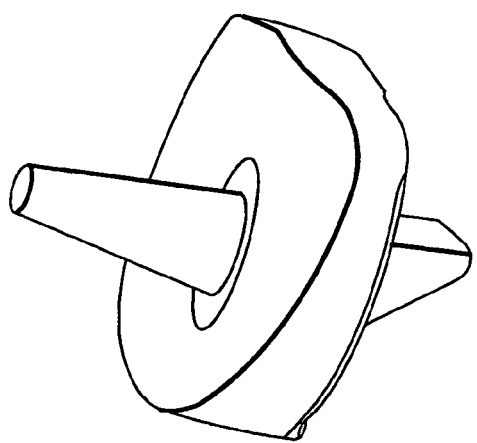
Figure 16A:
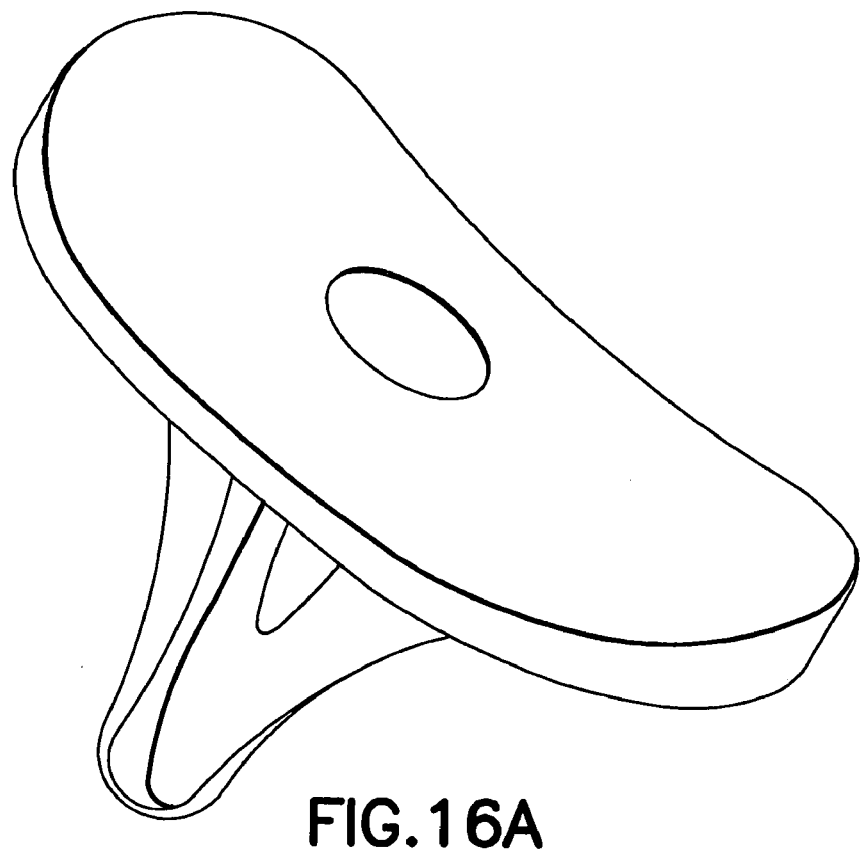
FIGS. 16A and 16B show perspective views (at various angles) of the superior surface of a tibial tray of a mobile bearing knee prosthesis according to an embodiment of the present invention.
Figure 16B:
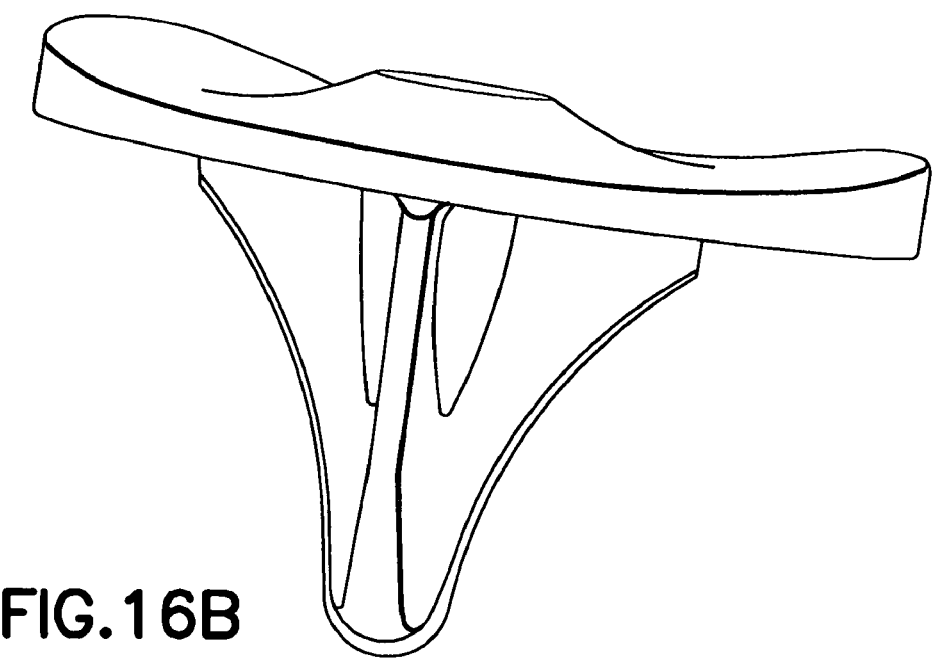

Referring now to FIGS. 12A and 12B it is seen that Mobile Bearing Knee 1200 according to an embodiment of the present invention may include Tibial Tray 1202 and Tibial Insert 1204. Of note, the design of these FIGS. 12A and 12B allows retention of the posterior cruciate ligament (PCL) via clearance for the PCL (which does not require posterior stabilization offered with the PS spine (e.g., as may be required on certain other embodiments)).

In another embodiment the tibial insert may be made of Ultra High Molecular Weight Polyethylene ("UHMWPE"). In one example (which example is intended to be illustrative and not restrictive) the UHMWPE may be molded UHMWPE (which, it is believed, wears at a lower rate than machined UHMWPE).

Referring now to FIGS. 13A-13F, 14A-14D, 15A-15C, 16A, 16B and 17A-17C, it is noted that under these embodiments of the present invention a mobile bearing knee prosthesis may include a bi-concave interface.

In this regard, it is noted that such a bi-concave interface may aid in providing an optimal anatomic configuration of the knee while at the same time providing a sufficiently thick (e.g., in terms of wear resistance) tibial insert articulation structure (e.g., polyethylene articulation structure). In one example (which example is intended to be illustrative and not restrictive), such articulation structure may be about 6.5 mm thick.

Figure 17A:
FIGS. 17A-17C show schematic cross-sectional views of a mobile bearing knee according to an embodiment of the present invention.
Figure 17B:
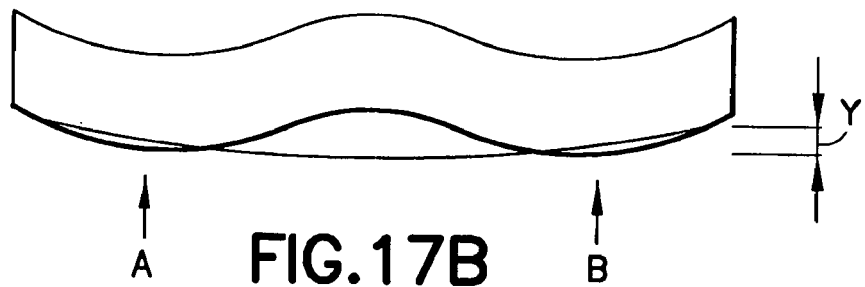

Further, referring in particular to FIG. 17A, it is seen that the tibial insert articulation structure may have a homogeneous, or constant, thickness (i.e., thickness "X" in this FIG. 17A) and referring in particular to FIG. 17B, it is seen that the tibial insert articulation structure may have a non-homogeneous, or non-constant, thickness (e.g., thicker by "Y" at the area marked "A" and "B" in this FIG. 17B).

Figure 17C:
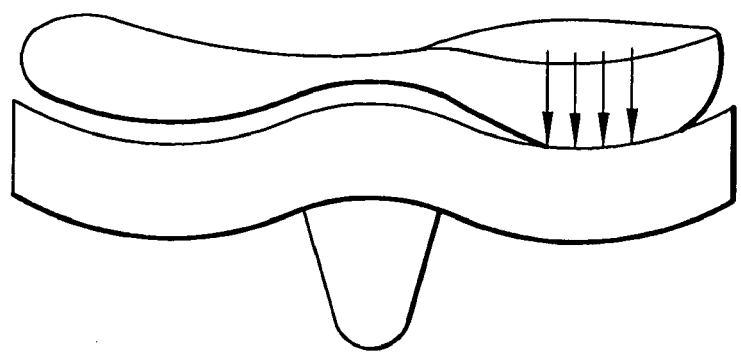

Further still, such a bi-concave interface may aid in coping with the potential shear stress provided by lift-off during movement by the patient (see FIG. 17C, showing an aspect of the invention directed to self-centering against lift-off and reduction or elimination of shear stress to the pivot feature (e.g., axial post)).

Of still further note, the embodiments of these FIGS. 13A-13F, 14A-14D, 15A-15C, 16A, 16B and 17A-17C may, of course, include some or all of the various pivoting, translating, locking, rotational constraint and/or control features described above.

Figure 18A:
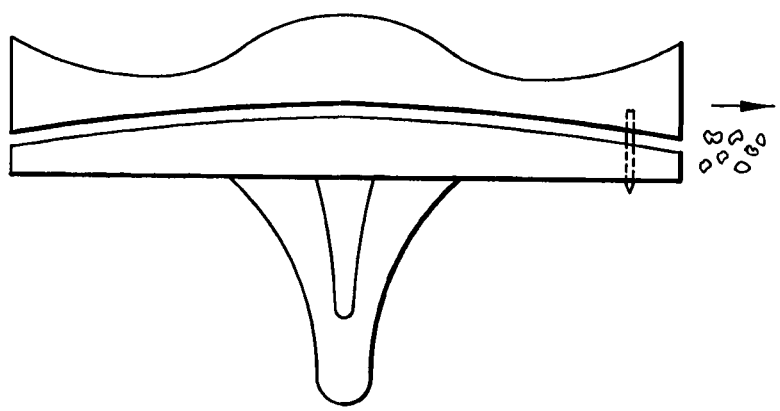
FIGS. 18A and 18B show schematic cross-sectional views of a mobile bearing knee according to an embodiment of the present invention.
Figure 18B:
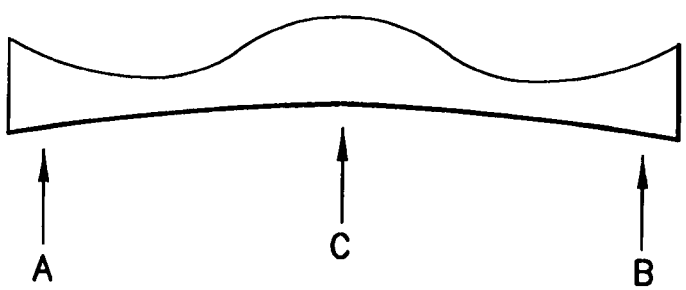

Referring now to FIGS. 18A and 18B, a mobile bearing knee prosthesis according to an embodiment of the present invention may include an interface (e.g., a spherical radius interface) comprised of a convex superior surface on the tibial tray and a concave inferior surface on the tibial insert (of note, such a spherical radius may have an inherent tendency to self-align).

Of note, the aforementioned configuration may help reduce wear at the interface between the tibial insert and the tibial tray by ejecting abrasive material (e.g., polyethylene particles created by relative movement at the interface) out from the interface (see FIG. 18A).

Of further note, as seen in FIG. 18B, the thickness of the material forming the tibial insert may vary as required (e.g., for optimum wear resistance vs. ease of movement). In one example (which example is intended to be illustrative and not restrictive), the areas marked "A" and "B" may be thicker than the area marked "C".

Of still further note, the embodiments of these FIGS. 18A and 18B may, of course, include some or all of the various pivoting, translating, locking, rotational constraint and/or control features described above.

Figures 19A, 19B:
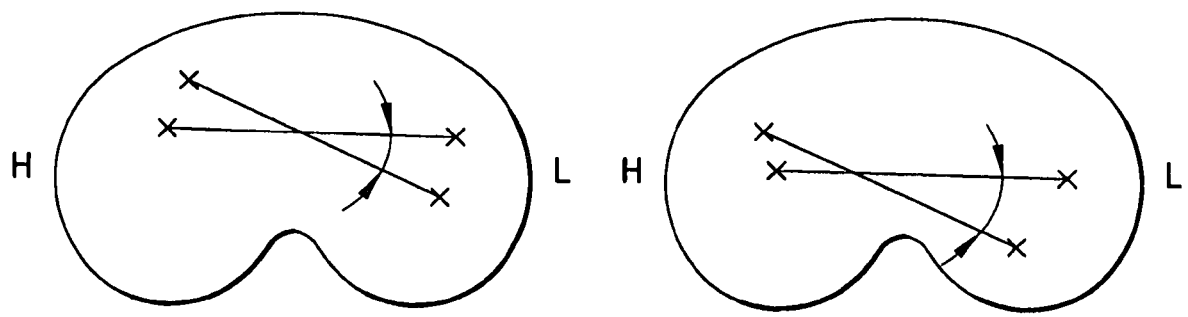
FIGS. 19A and 19B show schematic plan views of a centered pivoting feature (FIG. 19A) and an eccentered (or offset) pivoting feature (FIG. 19B) according to embodiments of the present invention.

Referring now to FIGS. 19A and 19B, it is again noted that a mobile bearing knee prosthesis according to the present invention may incorporate an eccentered (or offset) pivoting feature (e.g., axial post). More particularly, in one embodiment such an eccentered pivoting feature may serve (e.g., during movement by the patient) to decrease the anterior translation associated with the medial condolyte and increase the roll back (posterior translation) associated with the lateral condolyte. In this regard, see, for example, FIGS. 19A and 19B, where FIG. 19A shows the large anterior translation associated with a central pivot (e.g., at 70° of external rotation of the femur in relation to the tibia) and where FIG. 19B shows the smaller anterior translation associated with a medially offset pivot (e.g., at 70° of external rotation of the femur in relation to the tibia). More particularly, these FIGS. 19A and 19B show that the offset pivot results in a relatively smaller anterior translation associated with the medial condolyte and a relatively larger posterior translation associated with the lateral condolyte.

Further, it is noted that the embodiments of these FIGS. 19A and 19B may, of course, include some or all of the various pivoting, translating, locking, rotational constraint and/or control features described above.

Finally, referring now to FIGS. 20A-20E, it is noted that certain embodiments of the present invention relate to use of an offset pivot component (e.g., using an offset axial post) in association with other components which may otherwise be configured for use with a non-offset pivot component.

Figure 20A:
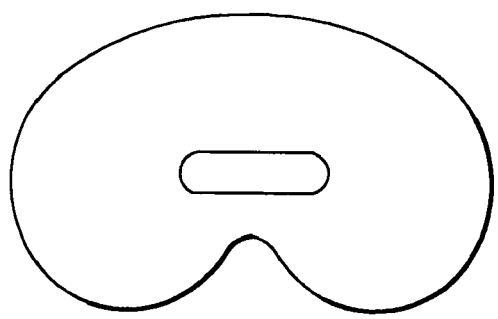
FIGS. 20A-20E show schematic plan views of offset pivot mechanisms according to embodiments of the present invention.
Figure 20B:
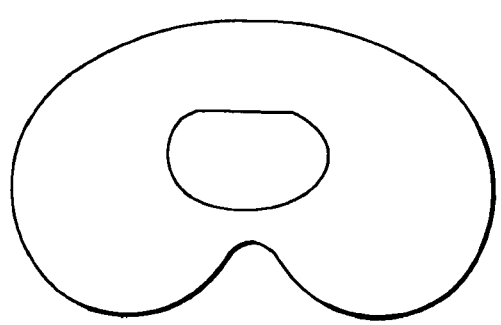
Figure 20C:
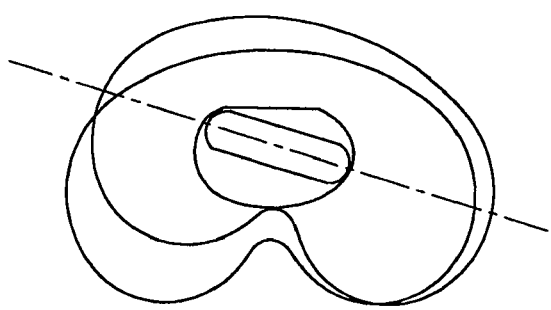
Figure 20D:
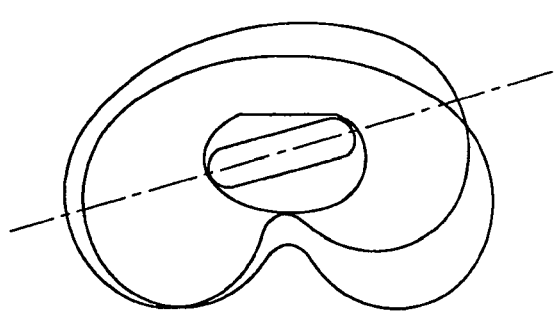

For example (which example is intended to be illustrative and not restrictive), an asymmetric component (e.g., offset axial post) may be utilized in association with a symmetric tibial tray and symmetric bearing (e.g., polyethylene bearing) to operate on a "cam" concept. FIG. 20A shows a plan view of a polyethylene bearing (under a no rotation condition) according to this embodiment and FIG. 20B shows a plan view of a tibial tray (under a no rotation condition) according to this embodiment. Further, FIG. 20C shows the eccentric center of rotation (at point A) associated with external rotation (right knee) and FIG. 20D shows the eccentric center of rotation (at point B) associated with external rotation (left knee).

Figure 20E:

Further, FIG. 20E shows a plan view utilizing a "Beam" shape.

Further still, it is noted that the embodiments of these FIGS. 20A-20E may include one or more internal stop mechanisms (e.g., for rotational constraint and/or control). Moreover, the embodiments of these FIGS. 20A-20E may be used in connection with a tibial insert and/or a tibial tray having an interface surface which includes flat, concave and/or convex portions.

Further still, it is noted that the embodiments of these FIGS. 20A-20E may, of course, include some or all of the various pivoting, translating, locking, rotational constraint and/or control features described above.

Of note, for the same size of knee prosthesis (e.g., size 3), the contact area between the tibial insert and the tibial tray may be higher for a "wave" design than for a flat design (e.g., ten percent higher contact area). Under certain circumstances, it may be desired to minimize this contact area.

Thus, in one embodiment, this contact area between the tibial insert and the tibial tray may be minimized by reducing the congruence factor of the second bearing (i.e., the interface between the tibial insert and the tibial tray in the mobile bearing knee as opposed to the interface between the tibial insert and the femoral component). It is noted that this solution is not possible for a flat design, for which the congruence factor is always equal to one. It is further noted that an advantage of the congruence factor approach is when contact only occurs on the loaded area.

In another embodiment, wear due to contact between the post and the hole may be decreased because shear stress is absorbed by the tibial tray (e.g., by the medial part of the "wave").

While a number of embodiments of the present invention have been described, it is understood that these embodiments are illustrative only, and not restrictive, and that many modifications may become apparent to those of ordinary skill in the art. For example, one or more appropriate fasteners may be used to assemble the mobile bearing knee prosthesis of the present invention (e.g., a screw or bolt to hold the tibial insert in correct orientation relative to the tibial tray). Further, the mobile bearing knee prosthesis of the present invention may provide a bearing which predicts position, self-aligns, and/or self-centers. Further still, the metal may be polished using any desired technique (e.g., a drill with polishing compound). Further still, the tibial insert may be smaller than the tibial tray (at least in certain dimensions) to prevent overhang during rotation (this may be accomplished, for example, by reducing the size of the medial/lateral aspect of the tibial insert). Further still, one or more of the mating articulating surfaces may be formed of poly, metal, diamond, ceramic, polyether ether ketone ("PEEK") and/or any other desired low friction articular materials. Further still, the tibial tray, the tibial insert and/or the femoral component may utilize, for example, a molded-on-metal configuration (e.g., UHMWP molded-on-metal). Further still, the tibial tray, the tibial insert and/or the femoral component may comprise, for example, cobalt chrome and/or titanium. Further still, the femoral component may interface with (e.g., be attached to) the femur of the patient using any desired mechanism (e.g., cement, one or more undercuts and matching protrusions, mechanical fasteners (e.g., screws), etc.). Further still, the tibial tray may interface with (e.g., be attached to) the tibia of the patient using any desired mechanism (e.g., cement, one or more undercuts and matching protrusions, mechanical fasteners (e.g., screws), etc.). Further still, one or more parts of the mobile bearing knee prosthesis according to the present invention may be used to "retrofit" existing prosthesis/components. Further still, the term "mobile bearing knee prosthesis" is, of course, intended to include (but not be limited to) "rotating platform" type mechanisms and "mensical bearing" type mechanisms.

What is claimed is:

1. A mobile bearing knee prosthesis, comprising:
a tibial tray for interfacing with a tibia of a patient;
a tibial insert disposed adjacent the tibial tray; and
a first cooperating element associated with a bottom surface of the tibial insert and a second cooperating element associated with an upper surface of the tibial tray;
wherein the tibial insert is capable of movement relative to the tibial tray and the movement of the tibial insert relative to the tibial tray includes at least pivotal movement;
wherein the pivotal movement is around an axis of rotation defined by a substantially circular raised location on the upper surface of the tibial tray;
wherein the substantially circular raised location curves downward from a top surface thereof along both a medial-lateral axis of the tibial tray and an anterior-posterior axis of the tibial tray;
wherein at least a portion of a medial edge of the tibial tray and at least a portion of a lateral edge of the tibial tray curve upward as the medial edge and the lateral edge are approached;
wherein the bottom surface of the tibial insert is configured to be substantially complementary to the upper surface of the tibial tray when the tibial insert and the tibial tray are aligned in both the medial-lateral axis and the anterior-posterior axis;
wherein the second cooperating element is provided at the substantially circular raised location on the upper surface of the tibial tray; and
wherein the first cooperating element comprises a post extending from the bottom surface of the tibial insert and the second cooperating element comprises a hole provided on the upper surface of the tibial tray.

* * * * *